(12) United States Patent
Shinozaki et al.

(10) Patent No.: US 7,259,297 B2
(45) Date of Patent: Aug. 21, 2007

(54) ENVIRONMENTAL STRESS-TOLERANT PLANTS

(75) Inventors: Kazuko Shinozaki, Ibaraki (JP); Mie Kasuga, Ibaraki (JP); Yoh Sakuma, Ibaraki (JP)

(73) Assignees: Independent Administrative Institute, Japan International Research Center for Agricultural Sciences, Ibaraki (JP); Incorporated Administrative Agency, National Agriculture and Bio-Oriented Research Organization, Ibaraki (JP)

( * ) Notice: Subject to any disclaimer, the term of this patent is extended or adjusted under 35 U.S.C. 154(b) by 323 days.

(21) Appl. No.: 10/887,475

(22) Filed: Jul. 8, 2004

(65) Prior Publication Data

US 2006/0015973 A1     Jan. 19, 2006

Related U.S. Application Data

(60) Continuation-in-part of application No. 10/664,741, filed on Sep. 19, 2003, which is a division of application No. 09/301,217, filed on Apr. 28, 1999, now Pat. No. 6,670,528.

(30) Foreign Application Priority Data

Oct. 14, 1998    (JP)                    10-292348

(51) Int. Cl.
     *C12N 15/29*      (2006.01)
     *C12N 15/82*      (2006.01)
     *A01H 5/00*      (2006.01)

(52) U.S. Cl. .................................... 800/298; 536/23.6
(58) Field of Classification Search .................. None
See application file for complete search history.

(56) References Cited

U.S. PATENT DOCUMENTS

| 5,891,859 | A | 4/1999 | Thomashow et al. |
| 6,417,428 | B1 * | 7/2002 | Thomashow et al. ....... 800/260 |
| 6,495,742 | B1 | 12/2002 | Shinozaki et al. |

OTHER PUBLICATIONS

Abe, et al., "Role of Arabidopsis MYC and MYB Homologs in Drought and Abscisic Acid-Regulated Gene Expression", The Plant Cell, vol. 9, pp. 1859-1868, Oct. 1997.

Abstract: Liu, Qiang, et al., Analysis of DREB Gene Encoding a Protein Binding to the cis-Element DRE which Stimulates Dehydration/Low Temperature Stress-Responsive Gene Expression in Arabidopsis Thaliana. 1998 Annual Meeting and the 38th Symposium of the Japanese Society of Plant Physiologists, May 3-5, 1998, F3a-11.

(Continued)

*Primary Examiner*—David H Kruse
(74) *Attorney, Agent, or Firm*—Davidson, Davidson & Kappel LLC

(57) ABSTRACT

The present invention relates to an environmental stress-tolerant plant. The invention discloses a transgenic plant containing a gene in which a DNA encodes a protein consisting of the amino acid sequence as shown in SEQ ID NO: 4 with the deletion of amino acids from positions 136-165 thereof, the DNA being operably linked downstream of a stress responsive promoter.

11 Claims, 14 Drawing Sheets
(7 of 14 Drawing Sheet(s) Filed in Color)

OTHER PUBLICATIONS

Abstract: Miura, Setsuko, et al., Analysis of Arabidopsis Thaliana, in which the Dehydration/Salt/Low-Temperature Stress Inducible Transcription Factor DREB1A or DREB2A is Over-expressed. 1998 Annual Meeting and the 38th Symposium of the Japanese Society of Plant Pathologists, May 3-5, 1998, F3a-12.

Abstract: Shirjwari, Zabta K., et al., Identification of the DREB1B Family Encoding Proteins which Bind to the Dehydration/Low Temperature Responsive Element DRE of Arabidopsis Thaliana and Analysis of Expression of the Family. 1998 Annual Meeting and the 38th Symposium of the Japanese Society of Plant Pathologists, May 3-5, 1998, F3a-13.

Busk, et al., "Regulatory elements in vivo in the promoter of the abscisic acid responsive gene reb 17 from maize", The Plant Journal, vol. 11, No. 6, 1997, pp. 1285-1295.

Jiang, et al., "Requirement of a CCGAC cis-acting element for cold induction of the BN115 gene from winter Brassica napus", Plant Molecular Biology, vol. 30, 1996, pp. 679-684.

Liu, et al., "Two Transcription Factors, DREB1 and DREB2, with an EREBP/AP2 DNA Binding Domain Sep. TwoCell. Signal Transduction Pathways in Drought-and Low-Temp-Respon. Gene Express., Respectively, in Arabidopsis", Aug. 1998, The Plant Cell, V. 10, p. 1391-1406.

Quellet, et al., "The wheat wcs 120 promoter is cold-inducible in both monocotyledonous and dicotyledonous species", Federation of European Biochemical Societies Letters, vol. 423, 1998, pp. 324-328.

Riechmann et al., "Arabidopsis transcription factors: genome-wide comparative analysis among eukaryotes", Science, Dec. 15, 2000, vol. 290, pp. 2105-2110.

Sambrook, et al., "Molecular Cloning, A Laboratory Manual", Second Edition, Cold Spring Harbor Laboratory Press, 1989, pp. 11.45-11.55.

Shinozaki, et al. "A Novel cis-Acting Element in an Arabidopsis Gene is involved in Responsiveness to Drought, Low-Temperature, or High-Salt Stress", The Plant Cell, vol. 6, pp. 251-264, Feb. 1994.

Shinwari, et al. "An Arabidopsis Gene Family Encoding DRE/CRT Binding Proteins Involved in Low-Temperature-Responsive Gene Expression", Biochemical and Biophysical Research Communication 250, pp. 161-170 (1998) Article No. RC 989267.

Yamaguchi-Shinozaki, Kazuko: Shinozaki, Kazuo; "A Novel cis-Acting Element in an Arabidopsis Gene is Involved in Responsiveness to Drought, Low-Temperature, or High-Salt Stress", The Plant Cell, vol. 6, 1994, pp. 251-264.

* cited by examiner

FIG. 3A
A
Effector Plasmid
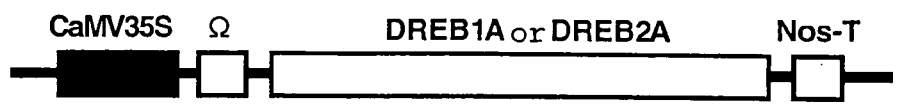
Reporter Plasmid
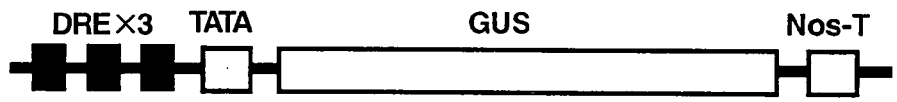
FIG. 3B
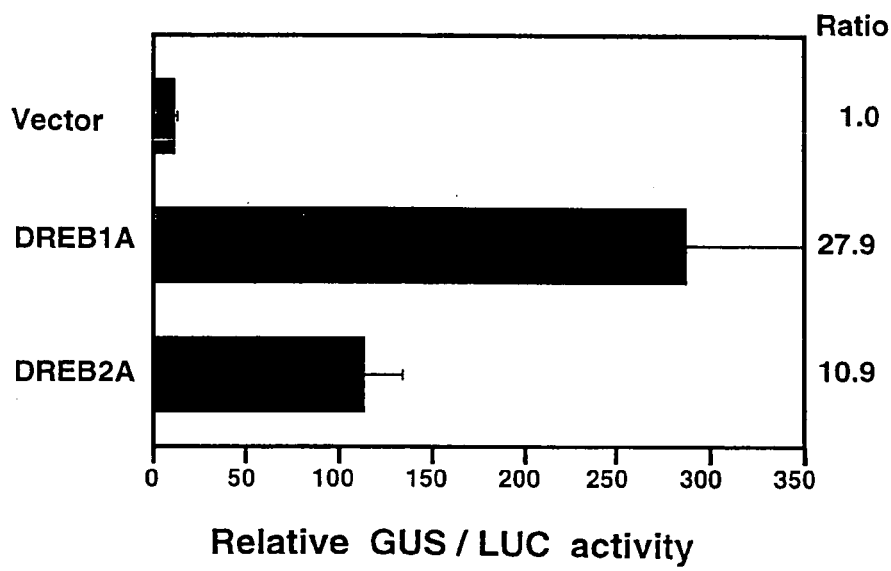

35S:DREB1A

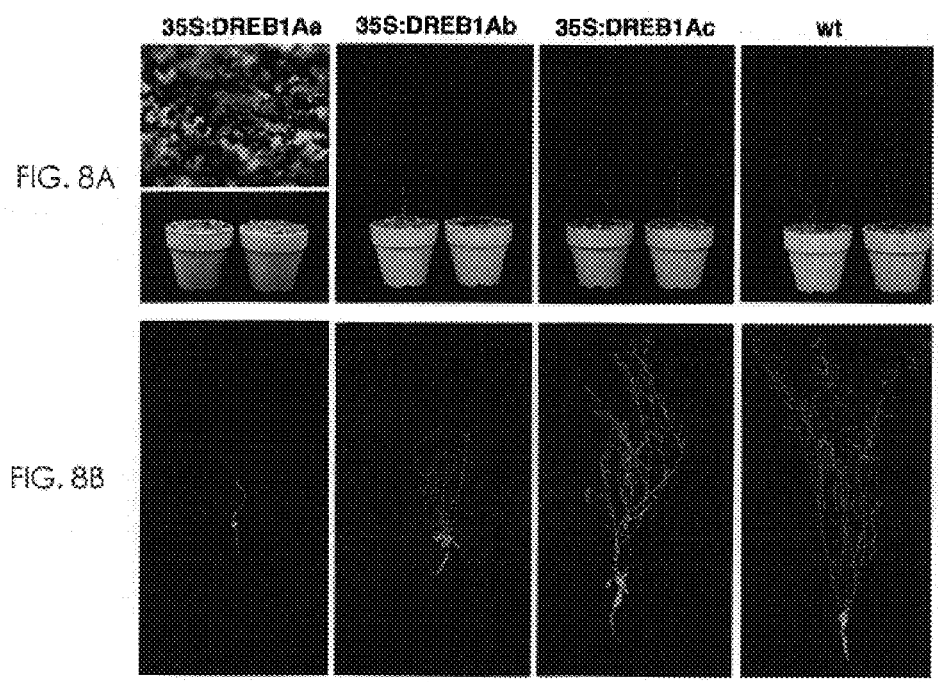

SEQUENCE LISTING

```
<160> NUMBER OF SEQ ID NOS: 75

<210> SEQ ID NO 1
<211> LENGTH: 933
<212> TYPE: DNA
<213> ORGANISM: Arabidopsis thaliana
<220> FEATURE:
<221> NAME/KEY: CDS
<222> LOCATION: (119)..(766)

<400> SEQUENCE: 1
cctgaactag aacagaaaga gagagaaact attatttcag caaaccatac caacaaaaaa      60
gacagagatc ttttagttac cttatccagt ttcttgaaac agagtactct tctgatca      118 atg aac tca ttt tct gct ttt tct gaa atg ttt ggc tcc gat tac gag      166
Met Asn Ser Phe Ser Ala Phe Ser Glu Met Phe Gly Ser Asp Tyr Glu
  1               5                  10                  15 tct tcg gtt tcc tca ggc ggt gat tat att ccg acg ctt gcg agc agc      214
Ser Ser Val Ser Ser Gly Gly Asp Tyr Ile Pro Thr Leu Ala Ser Ser
             20                  25                  30 tgc ccc aag aaa ccg gcg ggt cgt aag aag ttt cgt gag act cgt cac      262
Cys Pro Lys Lys Pro Ala Gly Arg Lys Lys Phe Arg Glu Thr Arg His
         35                  40                  45 cca ata tac aga gga gtt cgt cgg aga aac tcc ggt aag tgg gtt tgt      310
Pro Ile Tyr Arg Gly Val Arg Arg Arg Asn Ser Gly Lys Trp Val Cys
     50                  55                  60 gag gtt aga gaa cca aac aag aaa aca agg att tgg ctc gga aca ttt      358
Glu Val Arg Glu Pro Asn Lys Lys Thr Arg Ile Trp Leu Gly Thr Phe
 65                  70                  75                  80 caa acc gct gag atg gca gct cga gct cac gac gtt gcc gct tta gcc      406
Gln Thr Ala Glu Met Ala Ala Arg Ala His Asp Val Ala Ala Leu Ala
                 85                  90                  95 ctt cgt ggc cga tca gcc tgt ctc aat ttc gct gac tcg gct tgg aga      454
Leu Arg Gly Arg Ser Ala Cys Leu Asn Phe Ala Asp Ser Ala Trp Arg
            100                 105                 110 ctc cga atc ccg gaa tca act tgc gct aag gac atc caa aag gcg gcg      502
Leu Arg Ile Pro Glu Ser Thr Cys Ala Lys Asp Ile Gln Lys Ala Ala
        115                 120                 125 gct gaa gct gcg ttg gcg ttt cag gat gag atg tgt gat gcg acg acg      550
Ala Glu Ala Ala Leu Ala Phe Gln Asp Glu Met Cys Asp Ala Thr Thr
    130                 135                 140 gat cat ggc ttc gac atg gag gag acg ttg gtg gag gct att tac acg      598
Asp His Gly Phe Asp Met Glu Glu Thr Leu Val Glu Ala Ile Tyr Thr
```

```
                      145                 150                 155                 160
gcg gaa cag agc gaa aat gcg ttt tat atg cac gat gag gcg atg ttt       646
Ala Glu Gln Ser Glu Asn Ala Phe Tyr Met His Asp Glu Ala Met Phe
                    165                 170                 175 gag atg ccg agt ttg ttg gct aat atg gca gaa ggg atg ctt ttg ccg       694
Glu Met Pro Ser Leu Leu Ala Asn Met Ala Glu Gly Met Leu Leu Pro
                180                 185                 190 ctt ccg tcc gta cag tgg aat cat aat cat gaa gtc gac ggc gat gat       742
Leu Pro Ser Val Gln Trp Asn His Asn His Glu Val Asp Gly Asp Asp
            195                 200                 205 gac gac gta tcg tta tgg agt tat taaaactcag attattattt ccatttttag      796
Asp Asp Val Ser Leu Trp Ser Tyr
        210                 215 tacgatactt ttatttttat tattattttt agatcctttt ttagaatgga atcttcatta     856
tgtttgtaaa actgagaaac gagtgtaaat taaattgatt cagtttcagt ataaaaaaaa     916
aaaaaaaaaa aaaaaa                                                     933

<210> SEQ ID NO 2
<211> LENGTH: 216
<212> TYPE: PRT
<213> ORGANISM: Arabidopsis thaliana

<400> SEQUENCE: 2

Met Asn Ser Phe Ser Ala Phe Ser Glu Met Phe Gly Ser Asp Tyr Glu
 1               5                  10                  15

Ser Ser Val Ser Ser Gly Gly Asp Tyr Ile Pro Thr Leu Ala Ser Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Arg Asn Ser Gly Lys Trp Val Cys
    50                  55                  60

Glu Val Arg Glu Pro Asn Lys Lys Thr Arg Ile Trp Leu Gly Thr Phe
 65                  70                  75                  80

Gln Thr Ala Glu Met Ala Ala Arg Ala His Asp Val Ala Ala Leu Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Asp Ile Gln Lys Ala Ala
        115                 120                 125

Ala Glu Ala Ala Leu Ala Phe Gln Asp Glu Met Cys Asp Ala Thr Thr
    130                 135                 140

Asp His Gly Phe Asp Met Glu Glu Thr Leu Val Glu Ala Ile Tyr Thr
145                 150                 155                 160

Ala Glu Gln Ser Glu Asn Ala Phe Tyr Met His Asp Glu Ala Met Phe
                165                 170                 175

Glu Met Pro Ser Leu Leu Ala Asn Met Ala Glu Gly Met Leu Leu Pro
            180                 185                 190

Leu Pro Ser Val Gln Trp Asn His Asn His Glu Val Asp Gly Asp Asp
        195                 200                 205

Asp Asp Val Ser Leu Trp Ser Tyr
    210                 215

<210> SEQ ID NO 3
<211> LENGTH: 1437
<212> TYPE: DNA
<213> ORGANISM: Arabidopsis thaliana
```

```
<220> FEATURE:
<221> NAME/KEY: CDS
<222> LOCATION: (167)..(1171)

<400> SEQUENCE: 3
gctgtctgat aaaagaaga ggaaaactcg aaaaagctac acacaagaag aagaagaaaa      60
gatacgagca agaagactaa acacgaaagc gatttatcaa ctcgaaggaa gagactttga    120
ttttcaaatt tcgtccccta tagattgtgt tgtttctggg aaggag atg gca gtt      175
                                                  Met Ala Val
                                                   1 tat gat cag agt gga gat aga aac aga aca caa att gat aca tcg agg    223
Tyr Asp Gln Ser Gly Asp Arg Asn Arg Thr Gln Ile Asp Thr Ser Arg
        5                  10                  15 aaa agg aaa tct aga agt aga ggt gac ggt act act gtg gct gag aga    271
Lys Arg Lys Ser Arg Ser Arg Gly Asp Gly Thr Thr Val Ala Glu Arg
 20                  25                  30                  35 tta aag aga tgg aaa gag tat aac gag acc gta gaa gaa gtt tct acc    319
Leu Lys Arg Trp Lys Glu Tyr Asn Glu Thr Val Glu Glu Val Ser Thr
                 40                  45                  50 aag aag agg aaa gta cct gcg aaa ggg tcg aag aag ggt tgt atg aaa    367
Lys Lys Arg Lys Val Pro Ala Lys Gly Ser Lys Lys Gly Cys Met Lys
             55                  60                  65 ggt aaa gga gga cca gag aat agc cga tgt agt ttc aga gga gtt agg    415
Gly Lys Gly Gly Pro Glu Asn Ser Arg Cys Ser Phe Arg Gly Val Arg
         70                  75                  80 caa agg att tgg ggt aaa tgg gtt gct gag atc aga gag cct aat cga    463
Gln Arg Ile Trp Gly Lys Trp Val Ala Glu Ile Arg Glu Pro Asn Arg
     85                  90                  95 ggt agc agg ctt tgg ctt ggt act ttc cct act gct caa gaa gct gct    511
Gly Ser Arg Leu Trp Leu Gly Thr Phe Pro Thr Ala Gln Glu Ala Ala
100                 105                 110                 115 tct gct tat gat gag gct gct aaa gct atg tat ggt cct ttg gct cgt    559
Ser Ala Tyr Asp Glu Ala Ala Lys Ala Met Tyr Gly Pro Leu Ala Arg
                120                 125                 130 ctt aat ttc cct cgg tct gat gcg tct gag gtt acg agt acc tca agt    607
Leu Asn Phe Pro Arg Ser Asp Ala Ser Glu Val Thr Ser Thr Ser Ser
            135                 140                 145 cag tct gag gtg tgt act gtt gag act cct ggt tgt gtt cat gtg aaa    655
Gln Ser Glu Val Cys Thr Val Glu Thr Pro Gly Cys Val His Val Lys
        150                 155                 160 aca gag gat cca gat tgt gaa tct aaa ccc ttc tcc ggt gga gtg gag    703
Thr Glu Asp Pro Asp Cys Glu Ser Lys Pro Phe Ser Gly Gly Val Glu
    165                 170                 175 ccg atg tat tgt ctg gag aat ggt gcg gaa gag atg aag aga ggt gtt    751
Pro Met Tyr Cys Leu Glu Asn Gly Ala Glu Glu Met Lys Arg Gly Val
180                 185                 190                 195 aaa gcg gat aag cat tgg ctg agc gag ttt gaa cat aac tat tgg agt    799
Lys Ala Asp Lys His Trp Leu Ser Glu Phe Glu His Asn Tyr Trp Ser
                200                 205                 210 gat att ctg aaa gag aaa gag aaa cag aag gag caa ggg att gta gaa    847
Asp Ile Leu Lys Glu Lys Glu Lys Gln Lys Glu Gln Gly Ile Val Glu
            215                 220                 225 acc tgt cag caa caa cag cag gat tcg cta tct gtt gca gac tat ggt    895
Thr Cys Gln Gln Gln Gln Gln Asp Ser Leu Ser Val Ala Asp Tyr Gly
        230                 235                 240 tgg ccc aat gat gtg gat cag agt cac ttg gat tct tca gac atg ttt    943
Trp Pro Asn Asp Val Asp Gln Ser His Leu Asp Ser Ser Asp Met Phe
    245                 250                 255 gat gtc gat gag ctt cta cgt gac cta aat ggc gac gat gtg ttt gca    991
Asp Val Asp Glu Leu Leu Arg Asp Leu Asn Gly Asp Asp Val Phe Ala
```

-continued

| | | | | | | | | | | | | |
|---|---|---|---|---|---|---|---|---|---|---|---|---|
| Asp | Val | Asp | Glu | Leu | Leu | Arg | Asp | Leu | Asn | Gly | Asp | Val | Phe | Ala |
| 260 | | | | | 265 | | | | | 270 | | | | 275 |

```
ggc tta aat cag gac cgg tac ccg ggg aac agt gtt gcc aac ggt tca    1039
Gly Leu Asn Gln Asp Arg Tyr Pro Gly Asn Ser Val Ala Asn Gly Ser
            280                 285                 290 tac agg ccc gag agt caa caa agt ggt ttt gat ccg cta caa agc ctc    1087
Tyr Arg Pro Glu Ser Gln Gln Ser Gly Phe Asp Pro Leu Gln Ser Leu
        295                 300                 305 aac tac gga ata cct ccg ttt cag ctc gag gga aag gat ggt aat gga    1135
Asn Tyr Gly Ile Pro Pro Phe Gln Leu Glu Gly Lys Asp Gly Asn Gly
    310                 315                 320 ttc ttc gac gac ttg agt tac ttg gat ctg gag aac taaacaaaac         1181
Phe Phe Asp Asp Leu Ser Tyr Leu Asp Leu Glu Asn
325                 330                 335 aatatgaagc tttttggatt tgatatttgc cttaatccca caacgactgt tgattctcta  1241
tccgagtttt agtgatatag agaactacag aacacgtttt ttcttgttat aaaggtgaac  1301
tgtatatatc gaaacagtga tatgacaata gagaagacaa ctatagtttg ttagtctgct  1361
tctcttaagt tgttctttag atatgtttta tgttttgtaa caacaggaat gaataataca  1421
cacttgtaaa aaaaaa                                                  1437
```

<210> SEQ ID NO 4
<211> LENGTH: 335
<212> TYPE: PRT
<213> ORGANISM: Arabidopsis thaliana

<400> SEQUENCE: 4

| Met | Ala | Val | Tyr | Asp | Gln | Ser | Gly | Asp | Arg | Asn | Arg | Thr | Gln | Ile | Asp |
|---|---|---|---|---|---|---|---|---|---|---|---|---|---|---|---|
| 1 | | | | 5 | | | | | 10 | | | | | 15 | |

| Thr | Ser | Arg | Lys | Arg | Lys | Ser | Arg | Ser | Arg | Gly | Asp | Gly | Thr | Thr | Val |
|---|---|---|---|---|---|---|---|---|---|---|---|---|---|---|---|
| | | | 20 | | | | | 25 | | | | | 30 | | |

| Ala | Glu | Arg | Leu | Lys | Arg | Trp | Lys | Glu | Tyr | Asn | Glu | Thr | Val | Glu | Glu |
|---|---|---|---|---|---|---|---|---|---|---|---|---|---|---|---|
| | | 35 | | | | | 40 | | | | | 45 | | | |

| Val | Ser | Thr | Lys | Lys | Arg | Lys | Val | Pro | Ala | Lys | Gly | Ser | Lys | Lys | Gly |
|---|---|---|---|---|---|---|---|---|---|---|---|---|---|---|---|
| | 50 | | | | | 55 | | | | | 60 | | | | |

| Cys | Met | Lys | Gly | Lys | Gly | Pro | Glu | Asn | Ser | Arg | Cys | Ser | Phe | Arg |
|---|---|---|---|---|---|---|---|---|---|---|---|---|---|---|
| 65 | | | | 70 | | | | | 75 | | | | | 80 |

| Gly | Val | Arg | Gln | Arg | Ile | Trp | Gly | Lys | Trp | Val | Ala | Glu | Ile | Arg | Glu |
|---|---|---|---|---|---|---|---|---|---|---|---|---|---|---|---|
| | | | 85 | | | | | 90 | | | | | 95 | | |

| Pro | Asn | Arg | Gly | Ser | Arg | Leu | Trp | Leu | Gly | Thr | Phe | Pro | Thr | Ala | Gln |
|---|---|---|---|---|---|---|---|---|---|---|---|---|---|---|---|
| | | | 100 | | | | | 105 | | | | | 110 | | |

| Glu | Ala | Ala | Ser | Ala | Tyr | Asp | Glu | Ala | Ala | Lys | Ala | Met | Tyr | Gly | Pro |
|---|---|---|---|---|---|---|---|---|---|---|---|---|---|---|---|
| | | 115 | | | | | 120 | | | | | 125 | | | |

| Leu | Ala | Arg | Leu | Asn | Phe | Pro | Arg | Ser | Asp | Ala | Ser | Glu | Val | Thr | Ser |
|---|---|---|---|---|---|---|---|---|---|---|---|---|---|---|---|
| | 130 | | | | | 135 | | | | | 140 | | | | |

| Thr | Ser | Ser | Gln | Ser | Glu | Val | Cys | Thr | Val | Glu | Thr | Pro | Gly | Cys | Val |
|---|---|---|---|---|---|---|---|---|---|---|---|---|---|---|---|
| 145 | | | | | 150 | | | | | 155 | | | | | 160 |

| His | Val | Lys | Thr | Glu | Asp | Pro | Asp | Cys | Glu | Ser | Lys | Pro | Phe | Ser | Gly |
|---|---|---|---|---|---|---|---|---|---|---|---|---|---|---|---|
| | | | | 165 | | | | | 170 | | | | | 175 | |

| Gly | Val | Glu | Pro | Met | Tyr | Cys | Leu | Glu | Asn | Gly | Ala | Glu | Glu | Met | Lys |
|---|---|---|---|---|---|---|---|---|---|---|---|---|---|---|---|
| | | | 180 | | | | | 185 | | | | | 190 | | |

| Arg | Gly | Val | Lys | Ala | Asp | Lys | His | Trp | Leu | Ser | Glu | Phe | Glu | His | Asn |
|---|---|---|---|---|---|---|---|---|---|---|---|---|---|---|---|
| | | 195 | | | | | 200 | | | | | 205 | | | |

| Tyr | Trp | Ser | Asp | Ile | Leu | Lys | Glu | Lys | Glu | Lys | Gln | Lys | Glu | Gln | Gly |
|---|---|---|---|---|---|---|---|---|---|---|---|---|---|---|---|
| | 210 | | | | | 215 | | | | | 220 | | | | |

-continued

```
Ile Val Glu Thr Cys Gln Gln Gln Gln Asp Ser Leu Ser Val Ala
225                 230                 235                 240

Asp Tyr Gly Trp Pro Asn Asp Val Asp Gln Ser His Leu Asp Ser Ser
            245                 250                 255

Asp Met Phe Asp Val Asp Glu Leu Leu Arg Asp Leu Asn Gly Asp Asp
        260                 265                 270

Val Phe Ala Gly Leu Asn Gln Asp Arg Tyr Pro Gly Asn Ser Val Ala
    275                 280                 285

Asn Gly Ser Tyr Arg Pro Glu Ser Gln Gln Ser Gly Phe Asp Pro Leu
290                 295                 300

Gln Ser Leu Asn Tyr Gly Ile Pro Pro Phe Gln Leu Glu Gly Lys Asp
305                 310                 315                 320

Gly Asn Gly Phe Phe Asp Asp Leu Ser Tyr Leu Asp Leu Glu Asn
                325                 330                 335

<210> SEQ ID NO 5
<211> LENGTH: 937
<212> TYPE: DNA
<213> ORGANISM: Arabidopsis thaliana
<220> FEATURE:
<221> NAME/KEY: CDS
<222> LOCATION: (164)..(802)

<400> SEQUENCE: 5
cttgaaaaag aatctacctg aaaagaaaaa aagagagag agatataaat agctttacca      60
agacagatat actatctttt attaatccaa aaagactgag aactctagta actacgtact    120
acttaaacct tatccagttt cttgaaacag agtactctga tca atg aac tca ttt     175
                                              Met Asn Ser Phe
                                               1 tca gct ttt tct gaa atg ttt ggc tcc gat tac gag cct caa ggc gga     223
Ser Ala Phe Ser Glu Met Phe Gly Ser Asp Tyr Glu Pro Gln Gly Gly
  5                  10                  15                  20 gat tat tgt ccg acg ttg gcc acg agt tgt ccg aag aaa ccg gcg ggc     271
Asp Tyr Cys Pro Thr Leu Ala Thr Ser Cys Pro Lys Lys Pro Ala Gly
             25                  30                  35 cgt aag aag ttt cgt gag act cgt cac cca att tac aga gga gtt cgt     319
Arg Lys Lys Phe Arg Glu Thr Arg His Pro Ile Tyr Arg Gly Val Arg
         40                  45                  50 caa aga aac tcc ggt aag tgg gtt tct gaa gtg aga gag cca aac aag     367
Gln Arg Asn Ser Gly Lys Trp Val Ser Glu Val Arg Glu Pro Asn Lys
     55                  60                  65 aaa acc agg att tgg ctc ggg act ttc caa acc gct gag atg gca gct     415
Lys Thr Arg Ile Trp Leu Gly Thr Phe Gln Thr Ala Glu Met Ala Ala
 70                  75                  80 cgt gct cac gac gtc gct gca tta gcc ctc cgt ggc cga tca gca tgt     463
Arg Ala His Asp Val Ala Ala Leu Ala Leu Arg Gly Arg Ser Ala Cys
 85                  90                  95                 100 ctc aac ttc gct gac tcg gct tgg cgg cta cga atc ccg gag tca aca     511
Leu Asn Phe Ala Asp Ser Ala Trp Arg Leu Arg Ile Pro Glu Ser Thr
            105                 110                 115 tgc gcc aag gat atc caa aaa gcg gct gct gaa gcg gcg ttg gct ttt     559
Cys Ala Lys Asp Ile Gln Lys Ala Ala Ala Glu Ala Ala Leu Ala Phe
        120                 125                 130 caa gat gag acg tgt gat acg acg acc acg aat cat ggc ctg gac atg     607
Gln Asp Glu Thr Cys Asp Thr Thr Thr Thr Asn His Gly Leu Asp Met
    135                 140                 145 gag gag acg atg gtg gaa gct att tat aca ccg gaa cag agc gaa ggt     655
Glu Glu Thr Met Val Glu Ala Ile Tyr Thr Pro Glu Gln Ser Glu Gly
150                 155                 160
```

```
gcg ttt tat atg gat gag gag aca atg ttt ggg atg ccg act ttg ttg    703
Ala Phe Tyr Met Asp Glu Glu Thr Met Phe Gly Met Pro Thr Leu Leu
165                 170                 175                 180 gat aat atg gct gaa ggc atg ctt tta ccg ccg ccg tct gtt caa tgg    751
Asp Asn Met Ala Glu Gly Met Leu Leu Pro Pro Pro Ser Val Gln Trp
            185                 190                 195 aat cat aat tat gac ggc gaa gga gat ggt gac gtg tcg ctt tgg agt    799
Asn His Asn Tyr Asp Gly Glu Gly Asp Gly Asp Val Ser Leu Trp Ser
200                 205                 210 tac taatattcga tagtcgtttc cattttttgta ctatagtttg aaaatattct         852
Tyr agttcctttt tttagaatgg ttccttcatt ttattttatt ttattgttgt agaaacgagt   912
ggaaaataat tcaatacaaa aaaaa                                         937

<210> SEQ ID NO 6
<211> LENGTH: 213
<212> TYPE: PRT
<213> ORGANISM: Arabidopsis thaliana

<400> SEQUENCE: 6

Met Asn Ser Phe Ser Ala Phe Ser Glu Met Phe Gly Ser Asp Tyr Glu
1               5                   10                  15

Pro Gln Gly Gly Asp Tyr Cys Pro Thr Leu Ala Thr Ser Cys Pro Lys
            20                  25                  30

Lys Pro Ala Gly Arg Lys Lys Phe Arg Glu Thr Arg His Pro Ile Tyr
        35                  40                  45

Arg Gly Val Arg Gln Arg Asn Ser Gly Lys Trp Val Ser Glu Val Arg
    50                  55                  60

Glu Pro Asn Lys Lys Thr Arg Ile Trp Leu Gly Thr Phe Gln Thr Ala
65                  70                  75                  80

Glu Met Ala Ala Arg Ala His Asp Val Ala Ala Leu Ala Leu Arg Gly
                85                  90                  95

Arg Ser Ala Cys Leu Asn Phe Ala Asp Ser Ala Trp Arg Leu Arg Ile
            100                 105                 110

Pro Glu Ser Thr Cys Ala Lys Asp Ile Gln Lys Ala Ala Ala Glu Ala
        115                 120                 125

Ala Leu Ala Phe Gln Asp Glu Thr Cys Asp Thr Thr Thr Asn His
    130                 135                 140

Gly Leu Asp Met Glu Glu Thr Met Val Glu Ala Ile Tyr Thr Pro Glu
145                 150                 155                 160

Gln Ser Glu Gly Ala Phe Tyr Met Asp Glu Glu Thr Met Phe Gly Met
                165                 170                 175

Pro Thr Leu Leu Asp Asn Met Ala Glu Gly Met Leu Leu Pro Pro Pro
            180                 185                 190

Ser Val Gln Trp Asn His Asn Tyr Asp Gly Glu Gly Asp Gly Asp Val
        195                 200                 205

Ser Leu Trp Ser Tyr
    210

<210> SEQ ID NO 7
<211> LENGTH: 944
<212> TYPE: DNA
<213> ORGANISM: Arabidopsis thaliana
<220> FEATURE:
<221> NAME/KEY: CDS
<222> LOCATION: (135)..(782)
```

<400> SEQUENCE: 7

```
cctgaattag aaaagaaaga tagatagaga aataaatatt ttatcatacc atacaaaaaa      60
agacagagat cttctactta ctctactctc ataaaccttc tccagtttct gaaacagag     120 tactcttctg atca atg aac tca ttt tct gcc ttt tct gaa atg ttt ggc     170
              Met Asn Ser Phe Ser Ala Phe Ser Glu Met Phe Gly
                1               5                   10 tcc gat tac gag tct ccg gtt tcc tca ggc ggt gat tac agt ccg aag     218
Ser Asp Tyr Glu Ser Pro Val Ser Ser Gly Gly Asp Tyr Ser Pro Lys
         15                  20                  25 ctt gcc acg agc tgc ccc aag aaa cca gcg gga agg aag aag ttt cgt     266
Leu Ala Thr Ser Cys Pro Lys Lys Pro Ala Gly Arg Lys Lys Phe Arg
     30                  35                  40 gag act cgt cac cca att tac aga gga gtt cgt caa aga aac tcc ggt     314
Glu Thr Arg His Pro Ile Tyr Arg Gly Val Arg Gln Arg Asn Ser Gly
 45                  50                  55                  60 aag tgg gtg tgt gag ttg aga gag cca aac aag aaa acg agg att tgg     362
Lys Trp Val Cys Glu Leu Arg Glu Pro Asn Lys Lys Thr Arg Ile Trp
                 65                  70                  75 ctc ggg act ttc caa acc gct gag atg gca gct cgt gct cac gac gtc     410
Leu Gly Thr Phe Gln Thr Ala Glu Met Ala Ala Arg Ala His Asp Val
             80                  85                  90 gcc gcc ata gct ctc cgt ggc aga tct gcc tgt ctc aat ttc gct gac     458
Ala Ala Ile Ala Leu Arg Gly Arg Ser Ala Cys Leu Asn Phe Ala Asp
         95                 100                 105 tcg gct tgg cgg cta cga atc ccg gaa tca acc tgt gcc aag gaa atc     506
Ser Ala Trp Arg Leu Arg Ile Pro Glu Ser Thr Cys Ala Lys Glu Ile
    110                 115                 120 caa aag gcg gcg gct gaa gcc gcg ttg aat ttt caa gat gag atg tgt     554
Gln Lys Ala Ala Ala Glu Ala Ala Leu Asn Phe Gln Asp Glu Met Cys
125                 130                 135                 140 cat atg acg acg gat gct cat ggt ctt gac atg gag gag acc ttg gtg     602
His Met Thr Thr Asp Ala His Gly Leu Asp Met Glu Glu Thr Leu Val
                145                 150                 155 gag gct att tat acg ccg gaa cag agc caa gat gcg ttt tat atg gat     650
Glu Ala Ile Tyr Thr Pro Glu Gln Ser Gln Asp Ala Phe Tyr Met Asp
            160                 165                 170 gaa gag gcg atg ttg ggg atg tct agt ttg ttg gat aac atg gcc gaa     698
Glu Glu Ala Met Leu Gly Met Ser Ser Leu Leu Asp Asn Met Ala Glu
        175                 180                 185 ggg atg ctt tta ccg tcg ccg tcg gtt caa tgg aac tat aat ttt gat     746
Gly Met Leu Leu Pro Ser Pro Ser Val Gln Trp Asn Tyr Asn Phe Asp
    190                 195                 200 gtc gag gga gat gat gac gtg tcc tta tgg agc tat taaaattcga          792
Val Glu Gly Asp Asp Asp Val Ser Leu Trp Ser Tyr
205                 210                 215 tttttatttc cattttggt attatagctt tttatacatt tgatccttt ttagaatgga     852 tcttcttctt ttttggttg tgagaaacga atgtaaatgg taaagttgt tgtcaaatgc     912 aaatgttttt gagtgcagaa tatataatct tt                                 944
```

<210> SEQ ID NO 8
<211> LENGTH: 216
<212> TYPE: PRT
<213> ORGANISM: Arabidopsis thaliana

<400> SEQUENCE: 8

```
Met Asn Ser Phe Ser Ala Phe Ser Glu Met Phe Gly Ser Asp Tyr Glu
  1               5                  10                  15
```

-continued

```
Ser Pro Val Ser Ser Gly Gly Asp Tyr Ser Pro Lys Leu Ala Thr Ser
            20                  25                  30

Cys Pro Lys Lys Pro Ala Gly Arg Lys Lys Phe Arg Glu Thr Arg His
        35                  40                  45

Pro Ile Tyr Arg Gly Val Arg Gln Arg Asn Ser Gly Lys Trp Val Cys
    50                  55                  60

Glu Leu Arg Glu Pro Asn Lys Lys Thr Arg Ile Trp Leu Gly Thr Phe
65                  70                  75                  80

Gln Thr Ala Glu Met Ala Ala Arg Ala His Asp Val Ala Ala Ile Ala
                85                  90                  95

Leu Arg Gly Arg Ser Ala Cys Leu Asn Phe Ala Asp Ser Ala Trp Arg
            100                 105                 110

Leu Arg Ile Pro Glu Ser Thr Cys Ala Lys Glu Ile Gln Lys Ala Ala
        115                 120                 125

Ala Glu Ala Ala Leu Asn Phe Gln Asp Glu Met Cys His Met Thr Thr
    130                 135                 140

Asp Ala His Gly Leu Asp Met Glu Glu Thr Leu Val Glu Ala Ile Tyr
145                 150                 155                 160

Thr Pro Glu Gln Ser Gln Asp Ala Phe Tyr Met Asp Glu Glu Ala Met
                165                 170                 175

Leu Gly Met Ser Ser Leu Leu Asp Asn Met Ala Glu Gly Met Leu Leu
            180                 185                 190

Pro Ser Pro Ser Val Gln Trp Asn Tyr Asn Phe Asp Val Glu Gly Asp
        195                 200                 205

Asp Asp Val Ser Leu Trp Ser Tyr
    210                 215
```

```
<210> SEQ ID NO 9
<211> LENGTH: 1513
<212> TYPE: DNA
<213> ORGANISM: Arabidopsis thaliana
<220> FEATURE:
<221> NAME/KEY: CDS
<222> LOCATION: (183)..(1172)
<223> OTHER INFORMATION: n = a, g, t or c

<400> SEQUENCE: 9
```

| | | |
|---|---|---:|
| gagacgctag aaagaacgcg aaagcttgcg aagaagattt gcttttgatc gacttaacac | | 60 |
| gaacaacaaa caacatctgc gtgataaaga agagattttt gcctaaataa agaagagatt | | 120 |
| cgactctaat cctggagtta tcattcacga tagattctta gattgcgact ataaagaaga | | 180 |

```
ag atg gct gta tat gaa caa acc gga acc gag cag ccg aag aaa agg       227
   Met Ala Val Tyr Glu Gln Thr Gly Thr Glu Gln Pro Lys Lys Arg
   1               5                   10                  15 aaa tct agg gct cga gca ggt ggt tta acg gtg gct gat agg cta aag     275
Lys Ser Arg Ala Arg Ala Gly Gly Leu Thr Val Ala Asp Arg Leu Lys
            20                  25                  30 aag tgg aaa gag tac aac gag att gtt gaa gct tcg gct gtt aaa gaa     323
Lys Trp Lys Glu Tyr Asn Glu Ile Val Glu Ala Ser Ala Val Lys Glu
        35                  40                  45 gga gag aaa ccg aaa cgc aaa gtt cct gcg aaa ggg tcg aag aaa ggt     371
Gly Glu Lys Pro Lys Arg Lys Val Pro Ala Lys Gly Ser Lys Lys Gly
    50                  55                  60 tgt atg aag ggt aaa gga gga cca gat aat tct cac tgt agt ttt aga     419
Cys Met Lys Gly Lys Gly Gly Pro Asp Asn Ser His Cys Ser Phe Arg
65                  70                  75 gga gtt aga caa agg att tgg ggt aaa tgg gtt gca gag att cga gaa    467
Gly Val Arg Gln Arg Ile Trp Gly Lys Trp Val Ala Glu Ile Arg Glu
                85                  90                  95
```

|   |   |
|---|---|
| ccg aaa ata gga act aga ctt tgg ctt ggt act ttt cct acc gcg gaa<br>Pro Lys Ile Gly Thr Arg Leu Trp Leu Gly Thr Phe Pro Thr Ala Glu<br>80　　　　　　　　85　　　　　　　　90　　　　　　　　95<br>　　　　　　　　　　　　　　100　　　　　　　　　105　　　　　　　　110 | 515 |
| aaa gct gct tcc gct tat gat gaa gcg gct acc gct atg tac ggt tca<br>Lys Ala Ala Ser Ala Tyr Asp Glu Ala Ala Thr Ala Met Tyr Gly Ser<br>　　　　　　　115　　　　　　　　　120　　　　　　　　　125 | 563 |
| ttg gct cgt ctt aac ttc cct cag tct gtt ggg tct gag ttt act agt<br>Leu Ala Arg Leu Asn Phe Pro Gln Ser Val Gly Ser Glu Phe Thr Ser<br>　　　　130　　　　　　　　　135　　　　　　　　　140 | 611 |
| acg tct agt caa tct gag gtg tgt acg gtt gaa aat aag gcg gtt gtt<br>Thr Ser Ser Gln Ser Glu Val Cys Thr Val Glu Asn Lys Ala Val Val<br>145　　　　　　　　　150　　　　　　　　　155 | 659 |
| tgt ggt gat gtt tgt gtg aag cat gaa gat act gat tgt gaa tct aat<br>Cys Gly Asp Val Cys Val Lys His Glu Asp Thr Asp Cys Glu Ser Asn<br>160　　　　　　　　　165　　　　　　　　　170　　　　　　　　　175 | 707 |
| cca ttt agt cag att tta gat gtt aga gaa gag tct tgt gga acc agg<br>Pro Phe Ser Gln Ile Leu Asp Val Arg Glu Glu Ser Cys Gly Thr Arg<br>　　　　　　　　180　　　　　　　　　185　　　　　　　　　190 | 755 |
| ccg gac agt tgc acg gtt gga cat caa gat atg aat tct tcg ctg aat<br>Pro Asp Ser Cys Thr Val Gly His Gln Asp Met Asn Ser Ser Leu Asn<br>　　　　　　　195　　　　　　　　　200　　　　　　　　　205 | 803 |
| tac gat ttg ctg tta gag ttt gag cag cag tat tgg ggc caa gtt ttg<br>Tyr Asp Leu Leu Leu Glu Phe Glu Gln Gln Tyr Trp Gly Gln Val Leu<br>　　　　210　　　　　　　　　215　　　　　　　　　220 | 851 |
| cag gag aaa gag aaa ccg aag cag gaa gaa gag gag ata cag caa cag<br>Gln Glu Lys Glu Lys Pro Lys Gln Glu Glu Glu Glu Ile Gln Gln Gln<br>225　　　　　　　　　230　　　　　　　　　235 | 899 |
| caa cag gaa cag caa cag caa cag ctg caa ccg gat ttg ctt act gtt<br>Gln Gln Glu Gln Gln Gln Gln Gln Leu Gln Pro Asp Leu Leu Thr Val<br>240　　　　　　　　　245　　　　　　　　　250　　　　　　　　　255 | 947 |
| gca gat tac ggt tgg cct tgg tct aat gat att gta aat gat cag act<br>Ala Asp Tyr Gly Trp Pro Trp Ser Asn Asp Ile Val Asn Asp Gln Thr<br>　　　　　　　　260　　　　　　　　　265　　　　　　　　　270 | 995 |
| tct tgg gat cct aat gag tgc ttt gat att aat gaa ctc ctt gga gat<br>Ser Trp Asp Pro Asn Glu Cys Phe Asp Ile Asn Glu Leu Leu Gly Asp<br>　　　　　　　275　　　　　　　　　280　　　　　　　　　285 | 1043 |
| ttg aat gaa cct ggt ccc cat cag agc caa gac caa aac cac gta aat<br>Leu Asn Glu Pro Gly Pro His Gln Ser Gln Asp Gln Asn His Val Asn<br>　　　　290　　　　　　　　　295　　　　　　　　　300 | 1091 |
| tct ggt agt tat gat ttg cat ccg ctt cat ctc gag cca cac gat ggt<br>Ser Gly Ser Tyr Asp Leu His Pro Leu His Leu Glu Pro His Asp Gly<br>305　　　　　　　　　310　　　　　　　　　315 | 1139 |
| cac gag ttc aat ggt ttg agt tct ctg gat att tgagagttct gaggcaatgg<br>His Glu Phe Asn Gly Leu Ser Ser Leu Asp Ile<br>320　　　　　　　　　325　　　　　　　　　330 | 1192 |
| tcctacaaga ctacaacata atctttggat tgatcatagg agaaacaaga aataggtgtt | 1252 |
| aatgatctga ttcacaatga aaaatattt aataactcta tagttttgt tctttccttg | 1312 |
| gatcatgaac tgttgcttct catctattga gttaatatag cgaatagcag agtttctctc | 1372 |
| tttcttctct ttgtagaaaa aaaaaaaaaa aaaaaaaaaa aaaaaaayh sakmabgcar | 1432 |
| srcsdvsnaa nntrnatnar sarchcntrr agrctrascn csrcaswash tskbabarak | 1492 |
| aantamaysa kmasrngnga c | 1513 |

<210> SEQ ID NO 10
<211> LENGTH: 330
<212> TYPE: PRT
<213> ORGANISM: Arabidopsis thaliana

<400> SEQUENCE: 10

```
Met Ala Val Tyr Glu Gln Thr Gly Thr Glu Gln Pro Lys Lys Arg Lys
  1               5                  10                  15
Ser Arg Ala Arg Ala Gly Gly Leu Thr Val Ala Asp Arg Leu Lys Lys
             20                  25                  30
Trp Lys Glu Tyr Asn Glu Ile Val Glu Ala Ser Ala Val Lys Glu Gly
         35                  40                  45
Glu Lys Pro Lys Arg Lys Val Pro Ala Lys Gly Ser Lys Lys Gly Cys
     50                  55                  60
Met Lys Gly Lys Gly Gly Pro Asp Asn Ser His Cys Ser Phe Arg Gly
 65                  70                  75                  80
Val Arg Gln Arg Ile Trp Gly Lys Trp Val Ala Glu Ile Arg Glu Pro
                 85                  90                  95
Lys Ile Gly Thr Arg Leu Trp Leu Gly Thr Phe Pro Thr Ala Glu Lys
            100                 105                 110
Ala Ala Ser Ala Tyr Asp Glu Ala Ala Thr Ala Met Tyr Gly Ser Leu
            115                 120                 125
Ala Arg Leu Asn Phe Pro Gln Ser Val Gly Ser Glu Phe Thr Ser Thr
        130                 135                 140
Ser Ser Gln Ser Glu Val Cys Thr Val Glu Asn Lys Ala Val Val Cys
145                 150                 155                 160
Gly Asp Val Cys Val Lys His Glu Asp Thr Asp Cys Glu Ser Asn Pro
                165                 170                 175
Phe Ser Gln Ile Leu Asp Val Arg Glu Ser Cys Gly Thr Arg Pro
            180                 185                 190
Asp Ser Cys Thr Val Gly His Gln Asp Met Asn Ser Ser Leu Asn Tyr
        195                 200                 205
Asp Leu Leu Leu Glu Phe Glu Gln Gln Tyr Trp Gly Gln Val Leu Gln
    210                 215                 220
Glu Lys Glu Lys Pro Lys Gln Glu Glu Glu Ile Gln Gln Gln Gln
225                 230                 235                 240
Gln Glu Gln Gln Gln Gln Leu Gln Pro Asp Leu Leu Thr Val Ala
                245                 250                 255
Asp Tyr Gly Trp Pro Trp Ser Asn Asp Ile Val Asn Asp Gln Thr Ser
        260                 265                 270
Trp Asp Pro Asn Glu Cys Phe Asp Ile Asn Glu Leu Leu Gly Asp Leu
    275                 280                 285
Asn Glu Pro Gly Pro His Gln Ser Gln Asp Gln Asn His Val Asn Ser
290                 295                 300
Gly Ser Tyr Asp Leu His Pro Leu His Leu Glu Pro His Asp Gly His
305                 310                 315                 320
Glu Phe Asn Gly Leu Ser Ser Leu Asp Ile
                325                 330
```

<210> SEQ ID NO 11
<211> LENGTH: 30
<212> TYPE: DNA
<213> ORGANISM: Artificial Sequence
<220> FEATURE:
<223> OTHER INFORMATION: Designed oligonucleotide based on the promoter region of rd29 gene and having HindIII site.

<400> SEQUENCE: 11
aagcttaagc ttacatcagt ttgaaagaaa                                    30

<210> SEQ ID NO 12
<211> LENGTH: 31
<212> TYPE: DNA
<213> ORGANISM: Artificial Sequence
<220> FEATURE:
<223> OTHER INFORMATION: Designed oligonucleotide based on the promoter
      region of rd29A gene and having HindIII site.

<400> SEQUENCE: 12
aagcttaagc ttgcttttg gaactcatgt c                              31

<210> SEQ ID NO 13
<211> LENGTH: 32
<212> TYPE: DNA
<213> ORGANISM: Artificial Sequence
<220> FEATURE:
<223> OTHER INFORMATION: Designed oligonucleotide based on DREB1A gene
      and having BamHI site.

<400> SEQUENCE: 13
aagcttaagc ttgccataga tgcaattcaa tc                            32

<210> SEQ ID NO 14
<211> LENGTH: 36
<212> TYPE: DNA
<213> ORGANISM: Artificial Sequence
<220> FEATURE:
<223> OTHER INFORMATION: Designed oligonucleotide based on DREB1A gene
      and having BamHI site.

<400> SEQUENCE: 14
aagcttaagc ttttccaaag attttttct ttccaa                         36

<210> SEQ ID NO 15
<211> LENGTH: 30
<212> TYPE: DNA
<213> ORGANISM: Artificial Sequence
<220> FEATURE:
<223> OTHER INFORMATION: Designed oligonucleotide based on the promoter
      region of rd29A gene and having HindIII site.

<400> SEQUENCE: 15
ggatccggat ccatgaactc attttctgct                               30

<210> SEQ ID NO 16
<211> LENGTH: 32
<212> TYPE: DNA
<213> ORGANISM: Artificial Sequence
<220> FEATURE:
<223> OTHER INFORMATION: Designed oligonucleotide based on the promoter
      region of rd29A gene and having HindIII site.

<400> SEQUENCE: 16
ggatccggat ccttaataac tccataacga ta                            32

<210> SEQ ID NO 17
<211> LENGTH: 941
<212> TYPE: DNA
<213> ORGANISM: Arabidopsis thaliana

<400> SEQUENCE: 17
gccatagatg caattcaatc aaactgaaat ttctgcaaga atctcaaaca cggagatctc    60
aaagtttgaa agaaaattta tttcttcgac tcaaaacaaa cttacgaaat ttaggtagaa   120
cttatataca ttatattgta attttttgta acaaaatgtt tttattatta ttatagaatt   180

```
ttactggtta aattaaaaat gaatagaaaa ggtgaattaa gaggagagag gaggtaaaca      240
ttttcttcta ttttttcata ttttcaggat aaattattgt aaaagtttac aagatttcca      300
tttgactagt gtaaatgagg aatattctct agtaagatca ttatttcatc tacttctttt      360
atcttctacc agtagaggaa taaacaatat ttagctcctt tgtaaataca aattaattt       420 ccttcttgac atcattcaat tttaattta cgtataaaat aaaagatcat acctattaga       480
acgattaagg agaaatacaa ttcgaatgag aaggatgtgc cgtttgttat aataaacagc      540
cacacgacgt aaacgtaaaa tgaccacatg atgggccaat agacatggac cgactactaa      600
taatagtaag ttcattttta ggatggaata aatatcatac cgacatcagt tttgaaagaa      660
aagggaaaaa aagaaaaaat aaataaaaga tatactaccg acatgagttc caaaagcaa       720 aaaaaagat caagccgaca cagacacgcg tagagagcaa aatgactttg acgtcacacc       780
acgaaaacag acgcttcata cgtgtccctt tatctctctc agtctctcta taaacttagt      840
gagaccctcc tctgttttac tcacaaatat gcaaactaga aaacaatcat caggaataaa      900
gggtttgatt acttctattg gaaagaaaaa aatctttgga a                          941

<210> SEQ ID NO 18
<211> LENGTH: 71
<212> TYPE: DNA
<213> ORGANISM: Arabidopsis thaliana

<400> SEQUENCE: 18
cagtttgaaa gaaagggaa aaaagaaaa aataaataaa agatatacta ccgacatgag        60
ttccaaaaag c                                                           71

<210> SEQ ID NO 19
<211> LENGTH: 71
<212> TYPE: DNA
<213> ORGANISM: Artificial Sequence
<220> FEATURE:
<223> OTHER INFORMATION: Oligonucleotide having a partially mutated
      sequence within the DRE region.

<400> SEQUENCE: 19
cagtttgaaa gaaagggaa aaaagaaaa aataaataaa agatatattt tcgacatgag        60
ttccaaaaag c                                                           71

<210> SEQ ID NO 20
<211> LENGTH: 71
<212> TYPE: DNA
<213> ORGANISM: Artificial Sequence
<220> FEATURE:
<223> OTHER INFORMATION: Oligonucleotide having a partially mutated
      sequence within the DRE region.

<400> SEQUENCE: 20
cagtttgaaa gaaagggaa aaaagaaaa aataaataaa agatatacta cttttatgag        60
ttccaaaaag c                                                           71

<210> SEQ ID NO 21
<211> LENGTH: 71
<212> TYPE: DNA
<213> ORGANISM: Artificial Sequence
<220> FEATURE:
<223> OTHER INFORMATION: Oligonucleotide having a partially mutated
      sequence within the DRE region.

<400> SEQUENCE: 21
```
cagtttgaaa gaaaagggaa aaaaagaaaa aataaataaa agatatacta ccgacaaaag    60
ttccaaaaag c    71

<210> SEQ ID NO 22
<211> LENGTH: 71
<212> TYPE: DNA
<213> ORGANISM: Artificial Sequence
<220> FEATURE:
<223> OTHER INFORMATION: Oligonucleotide having a partially mutated
      sequence outside the DRE region.

<400> SEQUENCE: 22
cagtttgaaa gaaaagggaa aaaaagaaaa aataaataaa agatatacta ccgacatgat    60
caacaaaaag c    71

<210> SEQ ID NO 23
<211> LENGTH: 71
<212> TYPE: DNA
<213> ORGANISM: Artificial Sequence
<220> FEATURE:
<223> OTHER INFORMATION: Oligonucleotide having a partially mutated
      sequence outside the DRE region.

<400> SEQUENCE: 23
cagtttgaaa gaaaagggaa aaaaagaaaa aataaataaa agatatacta ccgacatgag    60
ttcggttaag c    71

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 24
ggggcggccg catggcagtt tatgatcaga g    31

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 25
tttgcggccg ctcactcgag ctgaaacgga ggta    34

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 26
ggggcggccg catggcagtt tatgatcaga g    31

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 27
tttgcggccg ctcaccggtc ctgatttaag cctg          34

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 28
ggggcggccg catggcagtt tatgatcaga g          31

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 29
tttgcggccg ctcacaagtg actctgatcc acat          34

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 30
ggggcggccg catggcagtt tatgatcaga g          31

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 31
tttgcggccg ctcactctgt tttcacatga acac          34

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 32
ggggcggccg catggcagtt tatgatcaga g          31

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 33
tttgcggccg ctcaagggaa attaagacga gcca          34

<210> SEQ ID NO 34
<211> LENGTH: 31
<212> TYPE: DNA

```
<213> ORGANISM: Artificial Sequence
<220> FEATURE:
<223> OTHER INFORMATION: Description of Artificial Sequence:primer

<400> SEQUENCE: 34
ggggcggccg catggcagtt tatgatcaga g                              31

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 35
ttcacaatct ggatcaggga aattaagacg                                30

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 36
ggggcggccg catggcagtt tatgatcaga g                              31

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 37
catgtctgaa gaatcctctg ttttcacatg                                30

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 38
ggggcggccg catggcagtt tatgatcaga g                              31

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 39
actgttcccc gggtacaagt gactctgatc                                30

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 40
ggggcggccg catggcagtt tatgatcaga g                              31
```

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 41
aatttagtcc tggccccttt cctaccatta                              30

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 42
ggggcggccg catggcagtt tatgatcaga g                            31

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 43
tcaaacatgt ctgaagaatc agggaaatta agacgagcca                   40

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 44
ggggcggccg catggcagtt tatgatcaga g                            31

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 45
ttcacaatct ggatcaggga aattaagacg                              30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 46
gggggatccg gattcttcag acatgtttga                              30

<210> SEQ ID NO 47
<211> LENGTH: 34
<212> TYPE: DNA
<213> ORGANISM: Artificial Sequence
<220> FEATURE:

-continued

<223> OTHER INFORMATION: Description of Artificial Sequence:primer

<400> SEQUENCE: 47
tttgcggccg ctcaccggtc ctgatttaag cctg                    34

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 48 ggggatccg gattcttcag acatgtttga                          30

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 49
tttgcggccg ctcactcgag ctgaaacgga ggta                    34

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 50 ggggatccg gattcttcag acatgtttga                          30

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 51
ggggcggccg ctttagttct ccagatccaa gt                      32

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 52
gggagatctc ggtctgatgc gtctgaggt                          29

<210> SEQ ID NO 53
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 53
tttgcggccg ctcacaagtg actctgatcc acat                    34

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 54
gggagatctc ggtctgatgc gtctgaggt                                29

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 55
ggggcggccg ctttagttct ccagatccaa gt                            32

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 56
gggagatctg gaaaggatgg taatggatt                                29

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 57
ggggcggccg ctttagttct ccagatccaa gt                            32

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 58
gggagatctg atccagattg tgaatctaa                                29

<210> SEQ ID NO 59
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 59
tttgcggccg ctcacaagtg actctgatcc acat                          34

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence:primer

```
<400> SEQUENCE: 60
gggagatctt acccggggaa cagtgttgc                                    29

<210> SEQ ID NO 61
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 61
tttgcggccg ctcactcgag ctgaaacgga ggta                              34

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 62
gggagatctt acccggggaa cagtgttgc                                    29

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 63
ggggcggccg ctttagttct ccagatccaa gt                                32

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 64
cgtcttaatt tccctgatcc agattgtgaa                                   30

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 65
ggggcggccg ctttagttct ccagatccaa gt                                32

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 66
catgtgaaaa cagaggattc ttcagacatg                                   30

<210> SEQ ID NO 67
<211> LENGTH: 32
```

```
<212> TYPE: DNA
<213> ORGANISM: Artificial Sequence
<220> FEATURE:
<223> OTHER INFORMATION: Description of Artificial Sequence:primer

<400> SEQUENCE: 67
ggggcggccg ctttagttct ccagatccaa gt                          32

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 68
gatcagagtc acttgtaccc ggggaacagt                             30

<210> SEQ ID NO 69
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 69
ggggcggccg ctttagttct ccagatccaa gt                          32

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 70
ttaaatcagg accgggaaa ggatggtaat                              30

<210> SEQ ID NO 71
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 71
ggggcggccg ctttagttct ccagatccaa gt                          32

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 72
tggctcgtct taatttccct gattcttcag acatgtttga                  40

<210> SEQ ID NO 73
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 73
```

-continued

```
<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 74
cgtcttaatt tccctgatcc agattgtgaa                                        30

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 75
tttgcggccg ctcactcgag ctgaaacgga ggta                                   34
```

```
ggggcggccg ctttagttct ccagatccaa gt                                     32
```

ENVIRONMENTAL STRESS-TOLERANT PLANTS

CROSS-REFERENCE TO RELATED APPLICATIONS

This application is a continuation-in-part of U.S. patent application Ser. No. 10/664,741, filed Sep. 19, 2003, which is a divisional of U.S. patent application Ser. No. 09/301,217, filed Apr. 28, 1999 and now U.S. Pat. No. 6,670,528 which claims priority benefit of Japanese Patent Application No. 292348/1998 filed Oct. 14, 1998, all of which are incorporated herein by reference.

BACKGROUND OF THE INVENTION

1. Field of the Invention

The present invention relates to a transgenic plant containing a gene in which a DNA encoding a protein that binds to dehydration responsive element (DRE) and regulates the transcription of genes located downstream of DRE is ligated downstream of a stress responsive promoter.

2. Prior Art

In the natural world, plants are living under various environmental stresses such as dehydration, high temperature, low temperature or salt. Unlike animals, plants cannot protect themselves from stresses by moving. Thus, plants have acquired various stress tolerance mechanisms during the courses of their evolution. For example, low temperature tolerant plants (*Arabidopsis thaliana*, spinach, lettuce, garden pea, barley, beet, etc.) have less unsaturated fatty acid content in their biomembrane lipid than low temperature sensitive plants (maize, rice, pumpkin, cucumber, banana, tomato, etc.). Therefore, even when the former plants are exposed to low temperatures, phase transition is hard to occur in their biomembrane lipid and, thus, low temperature injury does not occur easily.

To date, dehydration, low temperature or salt tolerant lines have been selected and crossed in attempts to artificially create environmental stress tolerant plants. However, a long time is needed for such selection, and the crossing method is only applicable between limited species. Thus, it has been difficult to create a plant with high environmental stress tolerance.

As biotechnology progressed recently, trials have been made to create dehydration, low temperature or salt tolerant plants by using transgenic technology which introduces into plants a specific, heterologous gene. Those genes which have been used for the creation of environmental stress tolerant plants include synthesis enzyme genes for osmoprotecting substances (mannitol, proline, glycine betaine, etc.) and modification enzyme genes for cell membrane lipid. Specifically, as the mannitol synthesis enzyme gene, *Escherichia coli*-derived mannitol 1-phosphate dehydrogenase gene [Science 259:508-510 (1993)] was used. As the proline synthesis enzyme gene, bean-derived $\Delta^1$-proline-5-carboxylate synthetase gene [Plant Physiol. 108:1387-1394 (1995)] was used. As the glycine betaine synthesis enzyme gene, bacterium-derived choline dehydrogenase gene [Plant J. 12:1334-1342 (1997)] was used. As the cell membrane lipid modification enzyme gene, *Arabidopsis thaliana*-derived ω-3 fatty acid desaturase gene [Plant Physiol. 105:601-605 (1994)] and blue-green alga-derived Δ9 desaturase gene [Nature Biotech. 14:1003-1006 (1996)] were used. However, the resultant plants into which these genes were introduced were instable in stress tolerance or low in tolerance level; none of them have been put into practical use to date.

Further, it is reported that a plurality of genes are involved in the acquisition of dehydration, low temperature or salt tolerance in plants [Plant Physiol., 115:327-334 (1997)]. Therefore, a gene encoding a transcription factor capable of activating simultaneously the expression of a plurality of genes involved in the acquisition of stress tolerance has been introduced into plants, yielding plants with high stress tolerance. However, when a gene which induces the expression of a plurality of genes is introduced into a host plant, the genes are activated at the same time. As a result, the energy of the host plant is directed to production of the products of these genes and intracellular metabolism of such gene products, which often brings about delay in the growth of the host plant or dwarfing of the plant.

OBJECTS AND SUMMARY OF THE INVENTION

It is an object of the present invention to provide a transgenic plant containing a gene in which a DNA encoding a protein that binds to a stress responsive element and regulates the transcription of genes located downstream of the element is ligated downstream of a stress responsive promoter, the transgenic plant having improved tolerance to environmental stresses (such as dehydration, low temperature and salt) and being free from dwarfing.

Toward the solution of the above problem, the present inventors have cloned a novel transcription factor gene that regulates the expression of genes involved in the acquisition of dehydration, low temperature or salt stress tolerance, and introduced into a plant this novel gene ligated downstream of a stress responsive promoter. As a result, the inventors have succeeded in creating a plant which has remarkably improved tolerance to dehydration, low temperature or salt and which is free from dwarfing. Thus, the present invention has been achieved.

The present invention relates to a transgenic plant containing a gene in which a DNA encoding the following protein (a) or (b) is ligated downstream of a stress responsive promoter:

(a) a protein consisting of the amino acid sequence as shown in SEQ ID NO: 2, SEQ ID NO: 4, SEQ ID NO: 6, SEQ ID NO: 8 or SEQ ID NO: 10;

(b) a protein which consists of the amino acid sequence having deletion, substitution or addition of at least one amino acid in the amino acid sequence as shown in SEQ ID NO: 2, SEQ ID NO: 4, SEQ ID NO: 6, SEQ ID NO: 8 or SEQ ID NO: 10 and which regulates the transcription of genes located downstream of a stress responsive element.

Further, the present invention relates to a transgenic plant containing a gene in which the following DNA (c) or (d) is ligated downstream of a stress responsive promoter:

(c) a DNA consisting of the nucleotide sequence as shown in SEQ ID NO: 1, SEQ ID NO: 3, SEQ ID NO: 5, SEQ ID NO: 7 or SEQ ID NO: 9;

(d) a DNA which hybridizes with the DNA consisting of the nucleotide sequence as shown in SEQ ID NO: 1, SEQ ID NO: 3, SEQ ID NO: 5, SEQ ID NO: 7 or SEQ ID NO: 9 under stringent conditions and which codes for a protein that regulates the transcription of genes located downstream of a stress responsive element.

Specific examples of the stress include dehydration stress, low temperature stress and salt stress.

As the stress responsive promoter, at least one selected from the group consisting of rd29A gene promoter, rd29B gene promoter, rd17 gene promoter, rd22 gene promoter, DREB1A gene promoter, cor6.6 gene promoter, cor15a gene promoter, erd1 gene promoter and kin1 gene promoter may be given.

This specification includes part or all of the contents as described in the specification and/or drawings of Japanese Patent Application No. 10-292348, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 presents diagrams showing the transcription activating ability of DREB1A and DREB2A proteins.

FIG. 8 presents photographs showing the growth of pBI35S:DREB1A-introduced transgenic plants (morphology of organisms).

(A) Shown are 30-day-old seedlings carrying the 35S-constitutive active form of the DREB2A construct with growth retardation (DREB2A CA-a, b and c), those carrying the 35S-full length DREB2A construct (DREB2A FL) and those carrying pBI121 (wt).
(B) Comparison of growth retardation among 5-week-old DREB2A related transgenic plants
(C) Close-up view of a plant carrying pBI 121 (wt) and a plant carrying the 35S:constitutive active form of DREB2A (DREB2A-a) shown in (B)
(D) RNA gel blot analysis of the DREB2A and rd29A genes in the transgenic plants

DETAILED DESCRIPTION OF THE INVENTION

Figure 1:
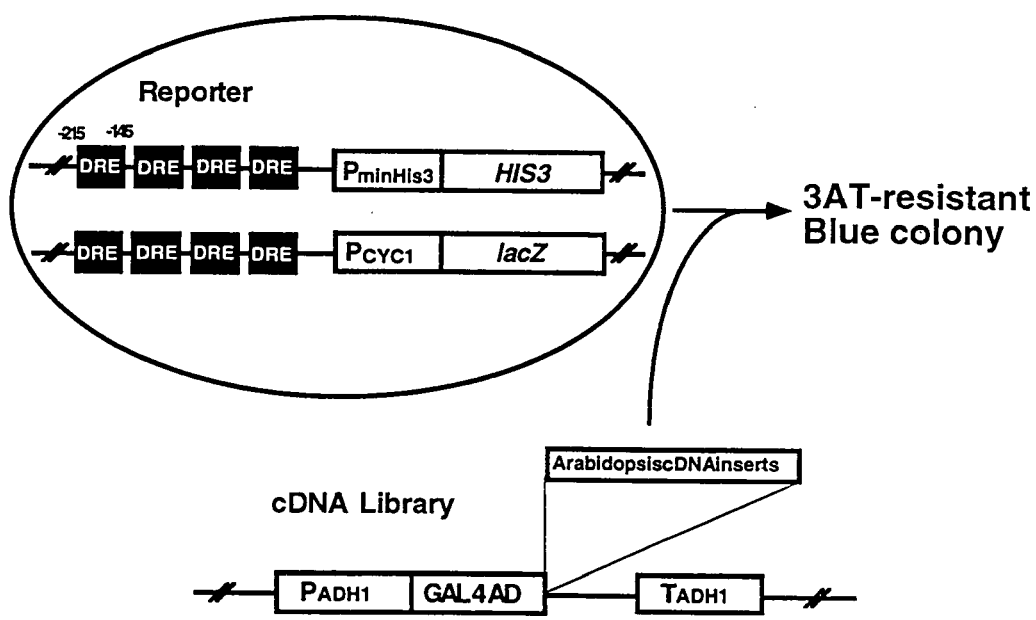
FIG. 1 is a diagram showing the principle of screening of DREB genes.

Hereinbelow, the present invention will be described in detail.

The transgenic plant of the invention is a environmental stress tolerant, transgenic plant created by introducing a gene in which a DNA (called "DREB gene") encoding a transcription factor that binds to a dehydration responsive element (DRE) and activates the transcription of genes located downstream of DRE is ligated downstream of a stress responsive promoter.

The DREB genes used in the invention can be cloned as described below. Of these DREB genes, DRE-binding protein 1A gene is called DREB1A gene; DRE-binding protein 1B gene is called DREB1B gene; DRE-binding protein 1C gene is called DREB1C gene; DRE-binding protein 2A gene is called DREB2A gene; and DRE-binding protein 2B gene is called DREB2B gene.

1. Cloning of DREB Gene 1-1. Preparation of mRNA and a cDNA Library from *Arabidopsis thaliana*

As a source of mRNA, a part of the plant of *Arabidopsis thaliana* such as leaves, stems, roots or flowers, or the plant as a whole may be used. Alternatively, the plant obtained by sowing seeds of *Arabidopsis thaliana* on a solid medium such as GM medium, MS medium or #3 medium and growing the resultant seedlings aseptically may be used. The mRNA level of DREB1A gene in *Arabidopsis thaliana* plants increases when they are exposed to low temperature stress (e.g. 10 to −4° C.). On the other hand, the mRNA level of DREB2A gene increases when plants are exposed to salt stress (e.g. 150-250 mM NaCl) or dehydration stress (e.g. dehydrated state). Therefore, *Arabidopsis thaliana* plants which have been exposed to such stress may also be used.

mRNA is prepared, for example, by exposing *Arabidopsis thaliana* plants grown on GM medium to the dehydration stress, low temperature stress or salt stress mentioned above and then freezing them with liquid nitrogen. Subsequently, conventional techniques for mRNA preparation may be used. For example, the frozen plant are ground in a mortar. From the resultant ground material, a crude RNA fraction is extracted by the glyoxal method, the guanidine thiocyanate-cesium chloride method, the lithium chloride-urea method, the proteinase K-deoxyribonuclease method or the like. From this crude RNA fraction, poly(A)$^+$ RNA (mRNA) can be obtained by the affinity column method using oligo dT-cellulose or poly U-Sepharose carried on Sepharose 2B or by the batch method. The resultant mRNA may further be fractionated by sucrose gradient centrifugation or the like.

Single-stranded cDNA is synthesized using the thus obtained mRNA as a template; this synthesis is performed using a commercial kit (e.g. ZAP-cDNA Synthesis Kit: Stratagene), oligo(dT)$_{20}$ and a reverse transcriptase. Then, double-stranded cDNA is synthesized from the resultant single-stranded cDNA. An appropriate adaptor such as EcoRI-NotI-BamHI adaptor is added to the resultant double-stranded cDNA, which is then ligated downstream of a transcriptional activation domain (such as GAL4 activation domain) in a plasmid (such as pAD-GAL4 plasmid: Stratagene) containing such a domain to thereby prepare a cDNA library.

1-2. A Host to be Used in the Cloning of DREB Gene

DREB gene can be cloned, for example, by one hybrid screening method using yeast. Screening by this method may be performed using a commercial kit (e.g. Matchmaker One Hybrid System: Clontech).

In the cloning of DREB gene using the above-mentioned kit, first, it is necessary to ligate a DNA fragment comprising DRE sequences to which a protein encoded by DREB gene (i.e. DREB protein) binds to both plasmids pHISi-1 and pLacZi contained in the kit. Then, the resultant plasmids are transformed into the yeast contained in the kit (*Saccharomayces cerevisiae* YM4271) to thereby prepare a host yeast for cloning.

The host yeast for cloning can biosynthesize histidine by the action of HIS3 protein which is expressed leakily by HIS3 minimum promoter. Thus, usually, this yeast can grow in the absence of histidine. However, since the promoter used for the expression of the gene encoding HIS3 protein is a minimum promoter which can only maintain the minimum transcription level, HIS3 protein produced in cells is extremely small in quantity. Therefore, when the host yeast is cultured in the presence of 3-AT (3-aminotriazole) that is a competitive inhibitor against HIS3 protein, the function of HIS3 protein in cells is inhibited by 3-AT in a concentration dependent manner. When the concentration of 3-AT exceeds a specific level, HIS3 protein in cells becomes unable to function and, as a result, the host yeast becomes unable to grow in the absence of histidine. Similarly, lacZ gene is also located downstream of CYC1 minimum promoter. Thus, β-galactosidase is produced only in extremely small quantity in the yeast cells. Therefore, when the host yeast is plated on an Xgal containing plate, colonies appearing thereon do not have such Xgal degrading ability that turns the colonies into blue as a whole. However, when a transcription factor that binds to DRE sequences located upstream of HIS3 and lacZ genes and activate the transcription thereof is expressed in the host yeast, the yeast becomes viable in the presence of a sufficient amount of 3-AT and, at the same time, Xgal is degraded to turn the colonies into blue.

As used herein, the term "dehydration responsive element (DRE)" refers to a cis-acting DNA domain consisting of a 9 bp conserved sequence 5'-TACCGACAT-3' located upstream of those genes which are expressed upon exposure to dehydration stress, low temperature stress, etc.

A DNA fragment comprising DRE can be obtained by amplifying the promoter region of rd29A gene (from −215 to −145 based on the translation initiation site of the gene) by polymerase chain reaction (PCR), rd29 gene being one of dehydration tolerance genes [Kazuko Yamaguchi-Shinozaki and Kazuo Shinozaki, The Plant Cell 6:251-264 (1994)]. As a template DNA which can be used in this PCR, genomic DNA from *Arabidopsis thaliana* is given. As a sense primer, 5'-aagcttaagcttacatcagtttgaaagaaa-3' (SEQ ID NO: 11) may be used. As an antisense primer, 5'-aagcttaagcttgcttttggaact-catgtc-3' (SEQ ID NO: 12) may be used. Other primers may also be used in the present invention.

1-3. Cloning of DREB1A Gene and DREB2A Gene

DREB1A gene and DREB2A gene can be obtained by transforming the cDNA library obtained in subsection 1-1 above into the host obtained in subsection 1-2 above by the lithium acetate method or the like, plating the resultant transformant on LB medium plate or the like containing Xgal (5-bromo-4-chloro-3-indolyl-β-D-galactoside) and 3-AT (3-aminotriazole), culturing the transformant, selecting blue colonies appearing on the plate and isolating the plasmids therefrom.

Briefly, a positive clone containing DREB1A gene or DREB2A gene contains a fusion gene composed of a DNA region coding for GAL4 activation domain (GAL4 AD) and a DNA region coding for a DRE-binding protein, and expresses a fusion protein (hybrid protein) composed of the DRE-binding protein and GAL4 activation domain under the control of alcohol dehydrogenase promoter. Subsequently, the expressed fusion protein binds, through the DRE-binding protein moiety, to DRE located upstream of a reporter gene. Then, GAL4 activation domain activates the transcription of lacZ gene and HIS3 gene. As a result, the positive clone produces remarkable amounts of HIS3 protein and β-galactosidase. Thus, because of the action of the HIS3 protein produced, the positive clone can biosynthesize histidine even in the presence of 3-AT. Therefore, the clone becomes viable in the presence of 3-AT and, at the same time, the Xgal in the medium is degraded by the β-galactosidase produced to turn the colonies into blue.

Subsequently, such blue colonies are subjected to single cell isolation, and the isolated cells are cultured. Then, plasmid DNA is purified from the cultured cells to thereby obtain DREB1A gene or DREB2A gene.

1-4. Homologues to DREB1A Protein or DREB2A Protein

Organisms may have a plurality of genes with similar nucleotide sequences which are considered to have evolved from a single gene. Proteins encoded by such genes are mutually called homologues. They can be cloned from the relevant gene library using as a probe a part of the gene of which the nucleotide sequence has already been known. In the present invention, genes encoding homologues to DREB1A or DREB2A protein can be cloned from the *Arabidopsis thaliana* cDNA library using DREB1A cDNA or DREB2A cDNA obtained in subsection 1-3 above as a probe.

1-5. Determination of Nucleotide Sequences

The cDNA portion is cut out from the plasmid obtained in subsection 1-3 or 1-4 above using a restriction enzyme and ligated to an appropriate plasmid such as pSK (Stratagene)

for sub-cloning. Then, the entire nucleotide sequence is determined. Sequencing can be performed by conventional methods such as the chemical modification method by Maxam-Gilbert or the dideoxynucleotide chain termination method using M13 phage. Usually, sequencing is carried out with an automated DNA sequencer (e.g. Perkin-Elmer Model 373A DNA Sequencer).

SEQ ID NO: 1 shows the nucleotide sequence of DREB1A gene, and SEQ ID NO: 2 the amino acid sequence of the protein encoded by this gene. SEQ ID NO: 3 shows the nucleotide sequence of DREB2A gene, and SEQ ID NO: 4 the amino acid sequence of the protein encoded by this gene. SEQ ID NO: 5 shows the nucleotide sequence of DREB1B gene, and SEQ ID NO: 6 the amino acid sequence of the protein encoded by this gene. SEQ ID NO: 7 shows the nucleotide sequence of DREB1C gene, and SEQ ID NO: 8 the amino acid sequence of the protein encoded by this gene. SEQ ID NO: 9 shows the nucleotide sequence of DREB2B gene, and SEQ ID NO: 10 the amino acid sequence of the protein encoded by this gene. As long as a protein consisting of one of the above-mentioned amino acid sequences has a function to bind to DRE to thereby activate the transcription of genes located downstream of DRE, the amino acid sequence may have mutation (such as deletion, substitution or addition) in at least one amino acid. A mutated gene coding for the protein having such mutated amino acid sequence may also be used in the present invention.

For example, at least 1 amino acid, preferably 1 to about 20 amino acids, more preferably 1 to 5 amino acids may be deleted in the amino acid sequence shown in SEQ ID NO: 2, 4, 6, 8 or 10; at least 1 amino acid, preferably 1 to about 20 amino acids, more preferably 1 to 5 amino acids may be added to the amino acid sequence shown in SEQ ID NO: 2, 4, 8 or 10; or at least 1 amino acid, preferably 1 to about 160 amino acids, more preferably 1 to 40 amino acids may be substituted with other amino acid(s) in the amino acid sequence shown in SEQ ID NO: 2, 4, 8 or 10. A gene coding for a protein having such mutated amino acid sequence may be used in the present invention as long as the protein has a function to bind to DRE to thereby activate the transcription of genes located downstream of DRE.

Also, a DNA which can hybridize with the above-mentioned gene under stringent conditions may be used in the present invention as long as the protein encoded by the DNA has a function to bind to DRE to thereby activate the transcription of genes located downstream of DRE. The "stringent conditions" means, for example, those conditions in which formamide concentration is 30-50%, preferably 50%, and temperature is 37-50° C., preferably 42° C.

A mutated gene may be prepared by known techniques such as the method of Kunkel, the gapped duplex method or variations thereof using a mutation introducing kit [e.g. Mutant-K (Takara) or Mutant-G (Takara)] or using LA PCR in vitro Mutagenesis Series Kit (Takara).

Once the nucleotide sequence of DREB gene has been determined definitely, the gene can be obtained by chemical synthesis, by PCR using the cDNA or genomic DNA of the gene as a template, or by hybridization with a DNA fragment having the above nucleotide sequence as a probe.

The recombinant vectors containing DREB1A gene and DREB2A gene, respectively, were introduced into *E. coli* K-12 strain and deposited at the National Institute of Bioscience and Human-Technology, Agency of Industrial Science and Technology (1-3, Higashi 1-Chome, Tsukuba City, Ibaraki, Japan) under accession numbers FERM BP-6654 (*E. coli* containing DREB1A gene) and FERM BP-6655 (*E. coli* containing DREB2A gene) on Aug. 11, 1998.

2. Determination of the DRE Binding Ability and Transcription Activating Ability of the Proteins Encoded by DREB Genes 2-1. Analysis of the DRE Binding Ability of the Proteins Encoded by DREB Genes The ability of the protein encoded by DREB gene (hereinafter referred to as the "DREB protein") to bind to DRE can be confirmed by performing a gel shift assay [Urao, T. et al., The Plant Cell 5:1529-1539 (1993)] using a fusion protein composed of the above protein and GST. A fusion protein composed of DREB1A protein and GST can be prepared as follows. First, DREB1A gene is ligated downstream of the GST coding region of a plasmid containing GST gene (e.g. pGEX-4T-1 vector: Pharmacia) so that the reading frames of the two genes coincide with each other. The resultant plasmid is transformed into *E. coli*, which is cultured under conditions that induce synthesis of the fusion protein. The resultant *E. coli* cells are disrupted by sonication, for example. Cell debris is removed from the disrupted material by centrifugation. Then, the supernatant is purified by affinity chromatography using a carrier such as glutathione-Sepharose to thereby obtain the fusion protein.

Gel shift assay is a method for examining the interaction between a DNA and a protein. Briefly, a DRE-containing DNA fragment labeled with $^{32}$P or the like is mixed with the fusion protein described above and incubated. The resultant mixture is electrophoresed. After drying, the gel is autoradiographed to detect those bands which have migrated behind as a result of the binding of the DNA fragment and the protein. In the present invention, the specific binding of DREB1A or DREB2A protein to the DRE sequence can be confirmed by making it clear that the above-mentioned behind band is not detected when a DNA fragment containing a varied DRE sequence is used.

2-2. Analysis of the Transcription Activating Ability of the Proteins Encoded by DREB Genes The transcription activating ability of the proteins encoded by DREB genes can be analyzed by a trans-activation experiment using a protoplast system from *Arabidopsis thaliana*. For example, DREB1A cDNA is ligated to pBI221 plasmid (Clontech) containing CaMV35S promoter to construct an effector plasmid. On the other hand, 3 cassettes of the DRE-containing 71 base DNA region obtained in subsection 1-2 above are connected tandemly to prepare a DNA fragment, which is then ligated upstream of TATA promoter located upstream of β-glucuronidase (GUS) gene in pBI221 plasmid to construct a reporter plasmid. Subsequently, these two plasmids are introduced into protoplasts of *Arabidopsis thaliana* and then GUS activity is determined. If GUS activity is increased by the simultaneous expression of DREB1A protein, it is understood that DREB1A protein expressed in the protoplasts is activating the transcription of GUS gene through the DRE sequence.

In the present invention, preparation of protoplasts and introduction of plasmid DNA into the protoplasts may be performed by the method of Abel et al. [Abel, S. et al., Plant J. 5:421-427 (1994)]. In order to minimize experimental errors resulted from the difference in plasmid DNA introduction efficiency by experiment, a plasmid in which luciferase gene is ligated downstream of CaMV35S promoter may be introduced into protoplasts together with the two plasmids described above, and β-glucuronidase activity against luciferase activity may be determined. Then, the determined value may be taken as a value indicating the transcription activating ability. β-glucuronidase activity can be determined by the method of Jefferson et al. [Jefferson, R. A. et al., EMBO J. 83:8447-8451 (1986)]; and luciferase activity can be determined using PicaGene Luciferase Assay Kit (Toyo Ink).

3. Creation of Transgenic Plants

A transgenic plant having tolerance to environmental stresses, in particular, low temperature stress (including freezing stress), dehydration stress and salt stress, can be created by introducing the gene obtained in section 1 above into a host plant using recombinant techniques. As a method for introducing the gene into a host plant, indirect introduction such as the *Agrobacterium* infection method, or direct introduction such as the particle gun method, polyethylene glycol method, liposome method, microinjection or the like may be used. When the *Agrobacterium* infection method is used, a transgenic plant can be created by the following procedures.

3-1. Preparation of a Recombinant Vector to be Introduced into a Plant and Transformation of *Agrobacterium*

A recombinant vector to be introduced into a plant can be prepared by digesting with an appropriate restriction enzyme a DNA comprising DREB1A, DREB1B, DREB1C, DREB2A or DREB2B gene obtained in section 1 above, ligating an appropriate linker to the resultant DNA if necessary, and inserting the DNA into a cloning vector for plant cells. As the cloning vector, a binary vector type plasmid such as pBI2113Not, pBI2113, pBI101, pBI121, pGA482, pGAH, pBIG; or an intermediate vector type plasmid such as pLGV23Neo, pNCAT, pMON200 may be used.

When a binary vector type plasmid is used, the gene of interest is inserted between the border sequences (LB, RB) of the binary vector. The resultant recombinant vector is amplified in *E. coli*. The amplified recombinant vector is introduced into *Agrobacterium tumefaciens* C58, LBA4404, EHA101, C58C1Rif$^R$, EHA105, etc. by freeze-thawing, electroporation or the like. The resultant *Agrobacterium tumefaciens* is used for the transduction of a plant of interest.

In addition to the method described above, the three-member conjugation method [Nucleic Acids Research, 12:8711 (1984)] may also be used to prepare DREB gene-containing *Agrobacterium* for use in plant infection. Briefly, an *E. coli* containing a plasmid comprising the gene of interest, an *E. coli* containing a helper plasmid (e.g. pRK2013) and an *Agrobacterium* are mixed and cultured on a medium containing rifampicin and kanamycin. Thus, a zygote *Agrobacterium* for use in plant infection can be obtained.

Since DREB gene encodes a protein which activates transcription, various genes are activated by the action of the expressed DREB protein in a DREB gene-introduced plant. This leads to increase in energy consumption and activation of metabolism in the plant. As a result, the growth of the plant itself may be inhibited. As a means to prevent such inhibition, it is considered to ligate a stress responsive promoter upstream of DREB gene so that the DREB gene is expressed only when a stress is loaded. Specific examples of such a promoter include the following ones:

rd29A gene promoter [Yamaguchi-Shinozaki, K. et al., The Plant Cell 6:251-264 (1994)];

rd29B gene promoter [Yamaguchi-Shinozaki, K. et al., The Plant Cell 6:251-264 (1994)];

rd17 gene promoter [Iwasaki, T. et al., Plant Physiol., 115:1287 (1997)];

rd22 gene promoter [Iwasaki, T. et al., Mol. Gen. Genet., 247:391-398 (1995)];

DREB1A gene promoter [Shinwari, Z. K. et al., Biochem. Biophys. Res. Com. 250:161-170 (1988)];

cor6.6 gene promoter [Wang, H. et al., Plant Mol. Biol. 28:619-634 (1995)];

cor15a gene promoter [Baker, S. S. et al., Plant Mol. Biol. 24:701-713 (1994)];

erd1 gene promoter [Nakashima K. et al., Plant J. 12:851-861 (1997)]; and kin1 gene promoter [Wang, H. et al., Plant Mol. Biol. 28:605-617 (1995)].

Other promoter may also be used as long as it is known to be stress responsive and to function in plant. These promoters can be obtained by PCR amplification using primers designed based on a DNA comprising the promoter and using relevant genomic DNA as a template.

If necessary, it is also possible to ligate a terminator which demands termination of transcription downstream of DREB gene. As the terminator, cauliflower mosaic virus-derived terminator or nopaline synthase gene terminater may be used. Other terminator may also be used as long as it is known to function in plant.

If necessary, an intron sequence which enhances the expression of a gene may be located between the promoter sequence and DREB gene. For example, the intron from maize alcohol dehydrogenase (Adh1) [Genes & Development 1:1183-1200 (1987)] may be introduced.

In order to select transformed cells of interest efficiently, it is preferable to use an effective selection marker gene in combination with DREB gene. As the selection marker, one or more genes selected from kanamycin resistance gene (NPTII), hygromycin phosphotransferase gene (htp) which confers resistance to the antibiotic hygromycin on plants, phosphinothricin acetyl transferase gene (bar) which confers resistance to bialaphos and the like. DREB gene and the selection marker gene may be incorporated together into a single vector. Alternatively, the two genes may be incorporated into separate vectors to prepare two recombinant DNAs.

3-2. Introduction of DREB Gene into a Host Plant

In the present invention, the term "host plant" means any of the following: cultured plant cells, the entire plant of a cultured plant, plant organs (such as leaves, petals, stems, roots, rhizomes, seeds), or plant tissues (such as epidermis, phloem, parenchyma, xylem, vascular bundle). Specific examples of plants which may be used as a host include *Arabidopsis thaliana*, tobacco, rice and maize.

DREB gene can be introduced into the above-described host plant by introducing a DREB gene-containing vector into plant sections by the *Agrobacterium* infection method, particle gun method or polyethylene glycol method. Alternatively, a DREB gene-containing vector may be introduced to protoplasts by electroporation.

If a gene of interest is introduced by the *Agrobacterium* infection method, a step of infecting a host plant with an *Agrobacterium* containing a plasmid comprising the gene of interest is necessary. This step can be performed by the vacuum infiltration method [CR Acad. Sci. Paris, Life Science, 316:1194 (1993)]. Briefly, *Arabidopsis thaliana* is grown in a soil composed of vermiculite and perlite (50:50). The resultant plant is dipped directly in a culture fluid of an *Agrobacterium* containing a plasmid comprising DREB gene, placed in a desiccator and then sucked with a vacuum pump to 65-70 mmHg. Then, the plant was allowed to stand at room temperature for 5-10 min. The plant pot is transferred to a tray and covered with a wrap to maintain the humidity. The next day, the wrap is removed. The plant is grown in that state to harvest seeds.

Subsequently, in order to select those individuals which have the gene of interest, seeds from various plant bodies are sown on MS agar medium supplemented with appropriate antibiotics. *Arabidopsis thaliana* grown on this medium are transferred to pots and grown there. As a result, seeds of a transgenic plant into which DREB gene is introduced can be obtained.

Generally, a transgene is located on the genome of the host plant. However, due to the difference in the locations on the genome, the expression of the transgene varies among transformants, presenting a phenomenon called position effect. Those transformants in which the transgene is expressed more highly can be selected by assaying mRNA levels in transformants by Northern blot analysis using a DNA fragment from the transgene as a probe.

The confirmation that the gene of interest is integrated in the transgenic plant of the invention and in the subsequent generation thereof can be made by extracting DNA from cells and tissues of those plants by conventional methods and detecting the transgene by PCR or Southern analysis known in the art.

3-3. Analysis of Expression Levels and Expression Sites of DREB Gene in Plant Tissues Expression levels and expression sites of DREB gene in a transgenic plant into which the gene is introduced can be analysed by extracting RNA from cells and tissues of the plant by conventional methods and detecting the mRNA of DREB gene by RT-PCR or Northern blot analysis known in the art. Alternatively, DREB protein may be analysed directly by Western blotting or the like using an antibody raised against the protein.

3-4. Changes in mRNA Levels of Various Genes in a Transgenic Plant in to which DREB Gene is Introduced It is possible to identify by Northern blot analysis those genes whose expression levels are believed to have been changed as a result of the action of DREB protein in a transgenic plant into which DREB gene is introduced. Northern blotting can assay those genes by comparing their mRNA levels in the transgenic plant into which DREB gene is introduced and in plants into which the gene is not introduced.

For example, plants grown on GM agar medium or the like are given dehydration and/or low temperature stress for a specific period of time (e.g. 1 to 2 weeks). Dehydration stress may be given by pulling out the plant from the agar medium and drying it on a filter paper for 10 min to 24 hr. Low temperature stress may be given by retaining the plant at 15 to −4° C. for 10 min to 24 hr. Total RNA is prepared from control plants which did not receive any stress and plants which received dehydration and low temperature stresses. The resultant total RNA is subjected to electrophoresis. Then, genes expressing are assayed by Northern blot analysis or RT-PCR.

3-5. Evaluation of the Tolerance to Environmental Stresses of the Transgenic Plant The tolerance to environmental stresses of the transgenic plant into which DREB gene is introduced can be evaluated by setting the plant in a pot containing a soil comprising vermiculite, perlite and the like exposing the plant to various stresses such as dehydration, low temperature and freezing, and examining the survival of the plant. For example, tolerance to dehydration stress can be evaluated by leaving the plant without giving water for 2 to 4 weeks and then examining the survival. Tolerance to freezing stress can be evaluated by leaving the plant at −6 to −10° C. for 5 to 10 days, growing it at 20 to 25° C. for 5 to 10 days and then examining its survival ratio.

PREFERRED EMBODIMENTS OF THE INVENTION

Hereinbelow, the present invention will be described more specifically with reference to the following Examples. However, the technical scope of the present invention is not limited to these Examples.

EXAMPLE 1

Cloning of DREB1A Gene and DREB2A Gene (1) Cultivation of *Arabidopsis thaliana* Plant

*Arabidopsis thaliana* seeds obtained from LEHLE SEEDS were sterilized in a solution containing 1% sodium hypochlorite and 0.02% Triton X-100 for 15 min. After rinsing with sterilized water, 40-120 seeds were sown on GM agar medium [4.6 g/L mixed salts for Murashige-Skoog medium (Nihon Pharmaceutical Co., Ltd.), 0.5 g/L MES, 30 g/L sucrose, 8 g/L agar, pH 5.7] and cultured at 22° C. under conditions of 16 hr light (about 1000 lux) 8 hr dark, to thereby obtain plant.

(2) Preparation of Poly(A)$^+$ RNA

The plant bodies obtained in (1) above were subjected to low temperature treatment at 4° C. for 24 hr, and then total RNA was prepared from them by the glyoxal method. Briefly, 3 g of *Arabidopsis thaliana* plant frozen in liquid nitrogen was suspended in 100 ml of 5.5 M GTC solution (5.5 M guanidine thiocyanate, 25 mM sodium citrate, 0.5% sodium N-lauroyl sarcosinate) and solubilized quickly with a homogenizer. This homogenate was sucked into and extruded from a syringe provided with a 18-G needle repeatedly more than 10 times to thereby disrupt the DNA. Then, the homogenate was centrifuged at 4° C. at 12,000×g for 15 min to precipitate and remove the cell debris.

The resultant supernatant was overlayered on 17 ml of CsTFA solution [a solution obtained by mixing cesium trifluoroacetate (Pharmacia), 0.25 M EDTA and sterilized water to give D=1.51] placed in an autoclaved centrifuge tube, and then ultracentrifuged in Beckmann SW28 Rotor at 15° C. at 25,000 rpm for 24 hr to precipitate RNA.

The resultant RNA was dissolved in 600 µl of 4 M GTC solution (obtained by diluting the above-described 5.5 M GTC solution with sterilized water to give a GTC concentration of 4 M) and precipitated with ethanol to thereby obtain total RNA of interest.

The resultant total RNA was dissolved in 2 ml of TE/NaCl solution (1:1 mixture of TE and 1 M NaCl) and passed through an oligo-dT cellulose column [prepared by packing a Bio-Rad Econocolumn (0.6 cm in diameter) with oligo-dT cellulose (type 3) (Collaborative Research) to a height of 1.5 cm] equilibrated with TE/NaCl in advance. The solution passed through the column was fed to the column again. Subsequently, the column was washed with about 8 ml of TE/NaCl. TE was added thereto to elute and purify poly(A)$^+$ RNA. The amount of the thus obtained RNA was determined with a UV spectroscope.

(3) Synthesis of a cDNA Library

Double-stranded cDNA was synthesized with a cDNA synthesis kit (Stratagene) using 5 μg of the poly(A)$^+$ RNA obtained in (2) above. Then, the double-stranded cDNA was ligated to pAD-GAL4 plasmid (Stratagene) to thereby synthesize a cDNA library. Briefly, at first, single-stranded cDNA was synthesized in the following reaction solution according to the protocol attached to the kit.

| | |
|---|---|
| Poly(A) + RNA | 5 μl (5 μg) |
| 10× 1st Strand synthesis buffer | 5 μl |
| DEPC-treated water | 34 μl |
| 40 U/μl Ribonuclease inhibitor | 1 μl |
| Nucleotide mix for 1st strand | 3 μl |
| 1.4 μg/μl Linker primer | 2 μl |
| Total | 50 μl |

To the above solution, 1.5 μl (50 U/μl) of reverse transcriptase was added and incubated at 37° C. for 1 hr to thereby synthesize single-stranded cDNA. To the resultant reaction solution containing single-stranded cDNA, the following reagents were added in the indicated order.

| | |
|---|---|
| Reaction solution containing single-stranded cDNA | 45 μl |
| 10× 2nd Strand synthesis buffer | 20 μl |
| NTP mix for 2nd strand | 6 μl |
| 1.5 U/μl RNase H | 2 μl |
| 9 U/μl DMA polymerase I | 11 μl |
| DEPC-treated water | 116 μl |
| Total | 200 μl |

The resultant reaction solution was incubated at 16° C. for 2.5 hr to thereby synthesize double-stranded cDNA.

The resultant double-stranded cDNA was blunt-ended by incubating it with 5 units of Pfu DNA polymerase at 72° C. for 30 min. Subsequently, the resultant cDNA was subjected to phenol/chloroform extraction and ethanol precipitation. To the resultant pellet, 9 μl of EcoRI-NotI-BamHI adaptor (Takara), 1 μl of 10× ligase buffer, 1 μl of ATP and 1 μl of T4 DNA ligase (4 U/μl) were added and incubated at 4° C. for 2 days to thereby add the adaptor to the double-stranded cDNA.

Subsequently, the cDNA having an EcoRI restriction enzyme site at both ends was ligated to the EcoRI site downstream of the GAL4 activation domain of pAD-GAL4 plasmid (Stratagene) (a cloning vector) with T4 DNA ligase to thereby synthesize a cDNA library.

(4) Preparation of Genomic DNA

Genomic DNA was prepared from the plant obtained in (1) above according to the method described by Maniatis, T. et al. [Molecular Cloning: A Laboratory Manual, pp. 187-198, Cold Spring Harbor Laboratory Press, Cold Spring Harbor, N.Y. (1982)]. Briefly, 2,000 ml of disruption buffer [0.35 M sucrose, 1 M Tris-HCl (pH 8.0), 5 mM MgCl$_2$, 50 mM KCl] was added to 50 g of *Arabidopsis thaliana* plant. The mixture was disrupted in a whirling blender for 1 min 3 times to homogenize the plant bodies.

The disrupted material was filtered to remove the cell residue. The filtrate was dispersed into centrifuge tubes and centrifuged in a swing rotor at 3,000×g at 4° C. for 10 min at a low speed. The resultant supernatant was discarded. The precipitate was suspended in 30 ml of ice-cooled disruption buffer and then re-centrifuged at a low speed. The same procedures were repeated 3 times until the green precipitate turned into white.

The resultant white precipitate was suspended in 10 ml of ice-cooled TE. To this suspension, 10 ml of lysis solution (0.2 M Tris-HCl (pH 8.0), 50 mM EDTA, 2% sodium N-lauroyl sarcosinate) was added. Then, 0.1 ml of proteinase K (10 mg/ml) was added thereto to digest nuclei. The resultant digest was subjected to phenol treatment and ethanol precipitation. The DNA fiber obtained by the precipitation was recovered by centrifugation at 3,000×g for 5 min and dissolved in 1 ml of TE to thereby obtain genomic DNA.

(5) Construction of a Host Yeast for Use in Yeast One Hybrid Screening

For the cloning of a gene encoding the transcription factor (DRE-binding protein) to be used in the invention, a host was constructed (FIG. 1). This host for cloning comprises two plasmids, one containing 4 cassettes of DRE motif-containing DNA upstream of HIS3 reporter gene and the other containing 4 cassettes of DRE motif-containing DNA upstream of lacZ reporter gene. Briefly, first, the promoter region of rd29A gene (the region from −215 to −145 based on the translation initiation point of rd29A gene) comprising DRE sequence to which the transcription factor to be used in the invention binds to was amplified by PCR. As a sense primer, 5'-aagcttaagcttacatcagtttgaaagaaa-3' (SEQ ID NO: 11) was synthesized. As an antisense primer, 5'-aagcttaagct-tgcttttggaactcatgtc-3' (SEQ ID NO: 12) was synthesized. To these primers, a HindIII restriction site was introduced to their 5'end so that PCR fragments can be ligated to a vector easily after amplification. These primers were synthesized chemically with a fully automated DNA synthesizer (Perkin-Elmer). A PCR was performed using these primers and the genomic DNA from (4) above as a template. The composition of the PCR reaction solution was as follows.

| | |
|---|---|
| Genomic DNA solution | 5 μl (100 ng) |
| Sterilized water | 37 μl |
| 10× PCR buffer [1.2 M Tris-HCl (pH 8.0), 100 mM KCl, 60 mM (NH$_4$)$_2$SO$_4$, 1% Triton X-100, 0.1 mg/ml BSA] | 5 μl |
| 50 pmol/μl Sense primer | 1 μl (50 pmol) |
| 50 pmol/μl Antisense primer | 1 μl (50 pmol) |
| KOD DNA polymerase (KOD-101, TOYOBO) | 1 μl (2.5 U) |
| Total | 50 μl |

After the above reaction solution was mixed thoroughly, 50 μl of mineral oil was overlayered on it. The PCR was performed 25 cycles, one cycle consisting of thermal denaturation at 98° C. for 15 sec, annealing at 65° C. for 2 sec and extension at 74° C. for 30 sec. After completion of the reaction, 50 μl of chloroform was added to the reaction solution, and then the resultant mixture was centrifuged at 4° C. at 15,000 rpm for 15 min. The resultant upper layer was recovered into a fresh microtube, to which 100 μl of ethanol was added and mixed well. The mixture was centrifuged at 4° C. at 15,000 rpm for 15 min to pellet the PCR product.

The resultant PCR product was digested with HindIII and then ligated to the HindIII site of vector pSK to yield a recombinant plasmid. This plasmid was transformed into *E. coli*. From the transformant, plasmid DNA was prepared to determine the nucleotide sequence. By these procedures, a transformant comprising pSK with a DNA fragment containing 4 cassettes of DRE connected in the same direction was selected.

The DNA fragment containing 4 cassettes of DRE was cut out from pSK plasmid using EcoRI and HincII, and then ligated to the EcoRI-MluI site upstream of the HIS3 minimum promoter of a yeast expression vector pHISi-1 (Clontech). Likewise, the DRE-containing DNA fragment was cut out from pSK plasmid using EcoRI and HincII, and then ligated to the EcoRI-SalI site upstream of the lacZ minimum promoter of a yeast expression vector pLacZi (Clontech). The resultant two plasmids were transformed into *Saccharomyces cerevisiae* YM4271 (MATa, ura3-52, his3-200, ade2-101, lys2-801, leu2-3, 112, trp1-903) (Clontech) to thereby yield a host yeast to be used in yeast one hybrid screening (FIG. 1).

(6) Cloning of DREB1A Gene and DREB2A Gene

The host yeast prepared in (5) above was transformed with the cDNA library prepared in (3) above. The resultant yeast transformants ($1.2 \times 10^6$) were cultured and screened as described previously. As a result, two positive clones were obtained. The cDNAs of these clones were cut out from pAD-GAL4 plasmid using EcoRI and then ligated to the EcoRI site of pSK plasmid to thereby obtain recombinant plasmids pSKDREB1A and pSKDREB2A.

(7) Determination of the Nucleotide Sequences

The entire nucleotide sequences for the cDNAs were determined using plasmids pSKDREB1A and pSKDREB2A. These plasmids were prepared with an automated plasmid preparation apparatus Model PI-100 (Kurabo). For the sequencing reaction, a reaction robot CATALYST 800 (Perkin Elmer) was used. For the DNA sequencing, Perkin Elmer Sequencer Model 373A was used. As a result, it was found that the cDNA from plasmid pSKDREB1A consists of 933 bp (SEQ ID NO: 1) and that only one open reading frame exists therein which encodes a protein consisting of 216 amino acid residues with a presumed molecular weight of about 24.2 kDa (SEQ ID NO: 2). On the other hand, it was found that the cDNA from plasmid pSKDREB2A consists of 1437 bp (SEQ ID NO: 3) and that only one open reading frame exists therein which encodes a protein consisting of 335 amino acid residues with a presumed molecular weight of about 37.7 kDa (SEQ ID NO: 4).

(8) Isolation of Genes Encoding Homologues to DREB1A or DREB2A Protein

Genes encoding homologues to the protein encoded by DREB1A or DREB2A gene obtained in (6) above were isolated. Briefly, genes encoding such homologues were isolated from *Arabidopsis thaliana* λgt11 cDNA library using as a probe a double-stranded cDNA fragment comprising DREB1A or DREB2A gene according to the method described by Sambrook, J. et al., Molecular Cloning: A Laboratory Manual 2nd Ed., Cold Spring Harbor Laboratory Press, NY (1989). As genes encoding homologues to DREB1A protein, DREB1B gene and DREB1C gene were obtained; as a gene encoding a homologue to DREB2A protein, DREB2B gene was obtained. As a result of DNA sequencing, it was found that DREB1B gene (SEQ ID NO: 5) was identical with the gene called CBF1 [Stockinger, E. J. et al., Proc. Natl. Acad. Sci. USA 94:1035-1040 (1997)], but DREB1C gene (SEQ ID NO: 7) and DREB2B gene (SEQ ID NO: 9) were found to be novel.

From the analysis of the open reading frame of DREB1C gene, it was found that the gene product encoded by this gene is a protein consisting of 216 amino acid residues with a molecular weight of about 24.3 kDa (SEQ ID NO: 8). Also, it was found that the gene product encoded by DREB2B gene is a protein consisting of 330 amino acid residues with a molecular weight of about 37.1 kDa (SEQ ID NO: 10).

EXAMPLE 2

Analysis of the DRE-Binding Ability of DREB1A and DREB2A Proteins

The ability of DREB1A and DREB2A proteins to bind to DRE was analyzed by preparing a fusion protein composed of glutathione-S-transferase (GST) and DREB1A or DREB2A protein using *E. coli* and then performing a gel shift assay. Briefly, the 429 bp DNA fragment from position 119 to position 547 of the nucleotide sequence of DREB1A cDNA or the 500 bp DNA fragment from position 167 to position 666 of the nucleotide sequence of DREB2A cDNA was amplified by PCR. Then, the amplified fragment was ligated to the EcoRI-SalI site of plasmid pGEX-4T-1 (Pharmacia). After the introduction of this plasmid into *E. coli* JM109, the resultant transformant was cultured in 200 ml of 2×YT medium (Molecular Cloning, (1982) Cold Spring Harbor Laboratory Press). To this culture, 1 mM isopropyl β-D-thiogalactoside which activates the promoter in plasmid pGEX-4T-1 was added to thereby induce the synthesis of a fusion protein of DREB1A (or DREB2A) and GST.

Figure 2A:
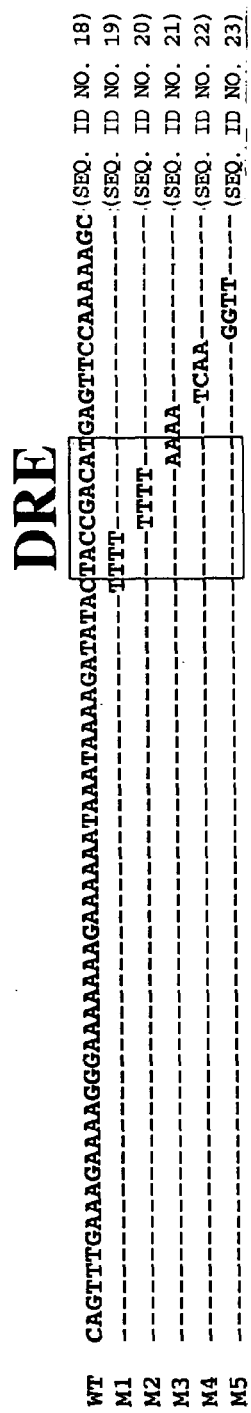
FIG. 2 shows the structures of probes used in a gel shift assay on the DRE-binding property of DREB1A and DREB2A proteins and presents electrophoresis photographs showing the results of the gel shift assay.
Figure 2B:
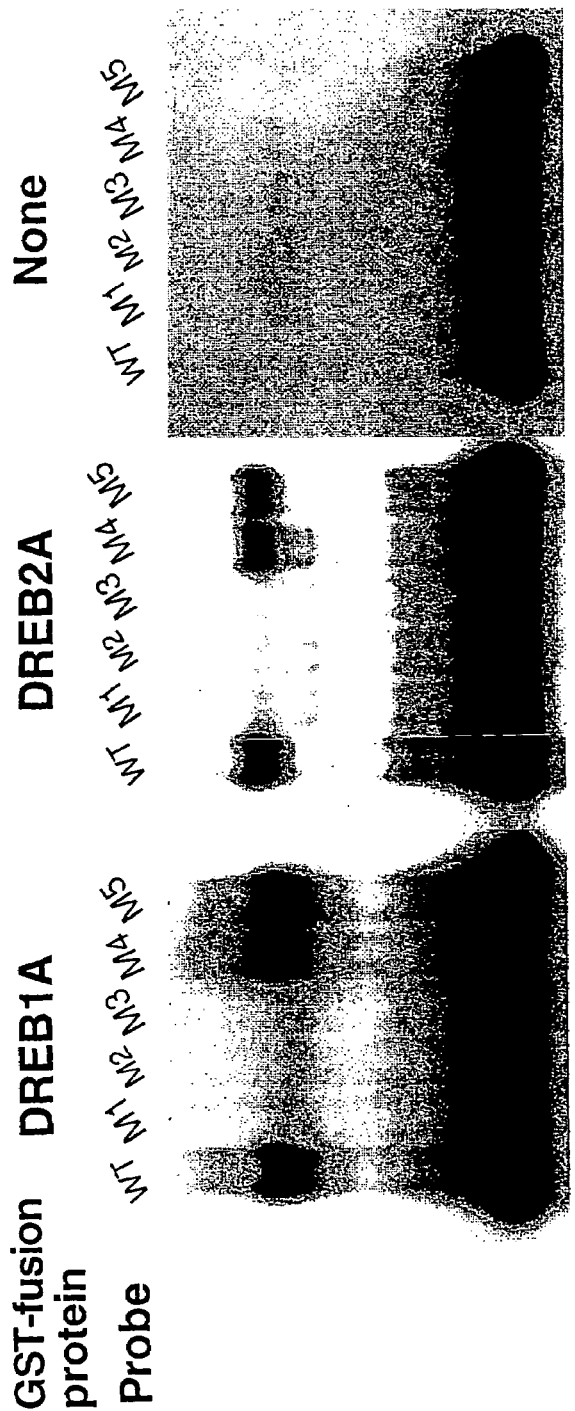

*E. coli* in which the fusion protein had been induced was suspended in 13 ml of buffer (10 mM Tris-HCl, 0.1 mM DTT, 0.1 mM phenylmethylsulfonyl fluoride). Then, 1% Triton X-100 and 1 mM EDTA were added thereto. After the cells were disrupted by sonication, the disrupted material was centrifuged at 22,000×g for 20 min. Then, the fusion protein of DREB1A (or DREB2A) and GST was purified by affinity chromatography using glutathione-Sepharose (Pharmacia) as a carrier. The resultant fusion protein was incubated with the DRE-containing 71 bp DNA fragment probe prepared by PCR and radiolabelled with $^{32}$P at room temperature for 20 min. This mixture was electrophoresed using 6% acryl amide gel containing 0.25× Tris-borate-EDTA at 100 V for 2 hr. FIG. 2 shows the results of autoradiogram on the gel after the electrophoresis. As is clear from this Figure, a band which migrated behind was detected when the fusion protein was incubated with the DRE-containing 71 bp DNA fragment probe (SEQ ID NO: 18). When a DNA fragment containing a varied DRE sequence (SEQ ID NO: 19, 20 or 21) was used, such a band was not detected. On the other hand, when a DNA fragment which was partly varied outside of DRE sequence (SEQ ID NO: 22 or 23) was used as a probe, a behind band was detected. Thus, it was shown that DREB1A or DREB2A protein specifically bound to DRE sequence.

EXAMPLE 3

Analysis of the Ability of DREB1A and DREB2A Proteins to Activate the Transcription of Genes Located Downstream of DRE In order to examine whether DREB1A and DREB2A proteins are able to trans-activate DRE-dependent transcription in plant cells, a trans-activation experiment was conducted using a protoplast system prepared from *Arabidopsis thaliana* leaves. Briefly, the cDNA of DREB1A or DREB2A was ligated to a pBI221 plasmid containing CaMV35S promoter to thereby construct an effector plasmid. On the other hand, 3 cassettes of the DRE-containing 71 bp DNA region were connected tandemly to prepare a DNA fragment, which was then ligated upstream to the minimum TATA promoter located upstream of β-glucuronidase (GUS) gene in a plasmid derived from pBI221 plasmid to construct a reporter plasmid. Subsequently, these two plasmids were introduced into protoplasts from *Arabidopsis thaliana* and then GUS activity was determined. When DREB1A or DREB2A protein was expressed simultaneously, GUS activity increased. This shows that DREB1A and DREB2A proteins are transcription factors which activate transcription through DRE sequence (FIG. 3).

EXAMPLE 4

Creation of a Transgenic Plant Containing a Gene in which a DNA Encoding DREB1A Protein is Ligated Downstream of CaMV35S Promoter (1) Construction of a Plant Plasmid Plasmid pSKDREB1A (10 µg) obtained as described above was digested with EcoRV (20 U) and SmaI (20 U) in a buffer containing 10 mM Tris-HCl (pH 7.5), 10 mM MgCl$_2$, 1 mM dithiothreitol (DTT) and 100 mM NaCl at 37° C. for 2 hr to thereby obtain a DNA fragment of about 0.9 kb containing DREB1A gene. On the other hand, plasmid pBI2113Not (10 µg) containing promoter DNA was digested with SmaI in a buffer containing 10 mM Tris-HCl (pH 7.5), 10 mM MgCl$_2$, 1 mM DTT and 100 mM NaCl at 37° C. for 2 hr. The 0.9 kb DNA fragment containing DREB1A gene and the digested pBI2113Not were treated with T4 DNA ligase (2 U) in a buffer [66 mM Tris-HCl (pH 7.6), 6.6 mM MgCl$_2$, 10 mM DTT, 0.1 mM ATP] at 15° C. for 16 hr for ligation. The ligated DNA was transformed into *E. coli* JM109. The transformant was cultured, and plasmid pBI35S:DREB1A was obtained from the culture. Then, the nucleotide sequence was determined, and those plasmids in which DREB1A gene was ligated in the sense direction were selected. Plasmid pBI2113Not mentioned above is a plasmid prepared by digesting pBI2113 [Plant Cell Physiology 37:49-59 (1996)] with SmaI and SacI to remove the coding region of GUS gene and ligating a SmaI-NotI-SacI polylinker to the resultant plasmid.

(2) Preparation of a Zygote *Agrobacterium* Containing the Plant Plasmid pBI35S:DREB1A

*E. coli* DH5α containing the plant plasmid pBI35S:DREB1A prepared in (1) above, *E. coli* HB101 containing helper plasmid pRK2013 and *Agrobacterium* C58 were cultured in mixture on LB agar medium at 28° C. for 24 hr. Grown colonies were scraped off and suspended in 1 ml of LB medium. This suspension (10 ml) was plated on LB agar medium containing 100 µg/ml rifampicin and 20 µg/ml kanamycin and cultured at 28° C. for 2 days to thereby obtain a zygote *Agrobacterium* C58 (pBI35S:DREB1A).

(3) Gene Transfer into *Arabidopsis thaliana* by *Agrobacterium* Infection

The resultant zygote *Agrobacterium* was cultured in 10 ml of LB medium containing 100 µg/ml rifampicin and 20 µg/ml kanamycin at 28° C. for 24 hr. Further, this culture fluid was added to 500 ml of LB medium and cultured for another 24 hr. The resultant culture fluid was centrifuged to remove the medium, and the cell pellet was suspended in 250 ml of LB medium.

On the other hand, 4 to 5 *Arabidopsis thaliana* plant bodies were grown in 9 cm pots containing soil composed of vermiculite and perlite (50:50) for 6 weeks. Then, the plant body was directly dipped in the LB culture fluid of the *Agrobacterium* containing plasmid pBI35S:DREB1A and placed in a desiccator, which was sucked with a vacuum pump to reduce the pressure to 650 mmHg and then left for 10 min. Subsequently, the plant pot was transferred to a tray and covered with a wrap to maintain the humidity. The next day, the wrap was removed. Thereafter, the plant was grown uncovered to thereby obtain seeds. After sterilization in an aqueous solution of sodium hypochlorite, the seeds were sown on an agar medium for selection (MS medium supplemented with 100 µg/ml vancomycin and 30 µg/ml kanamycin). *Arabidopsis thaliana* seedlings grown on this medium were transplanted to pots and grown there to obtain seeds of the transformed plant.

Figure 5:
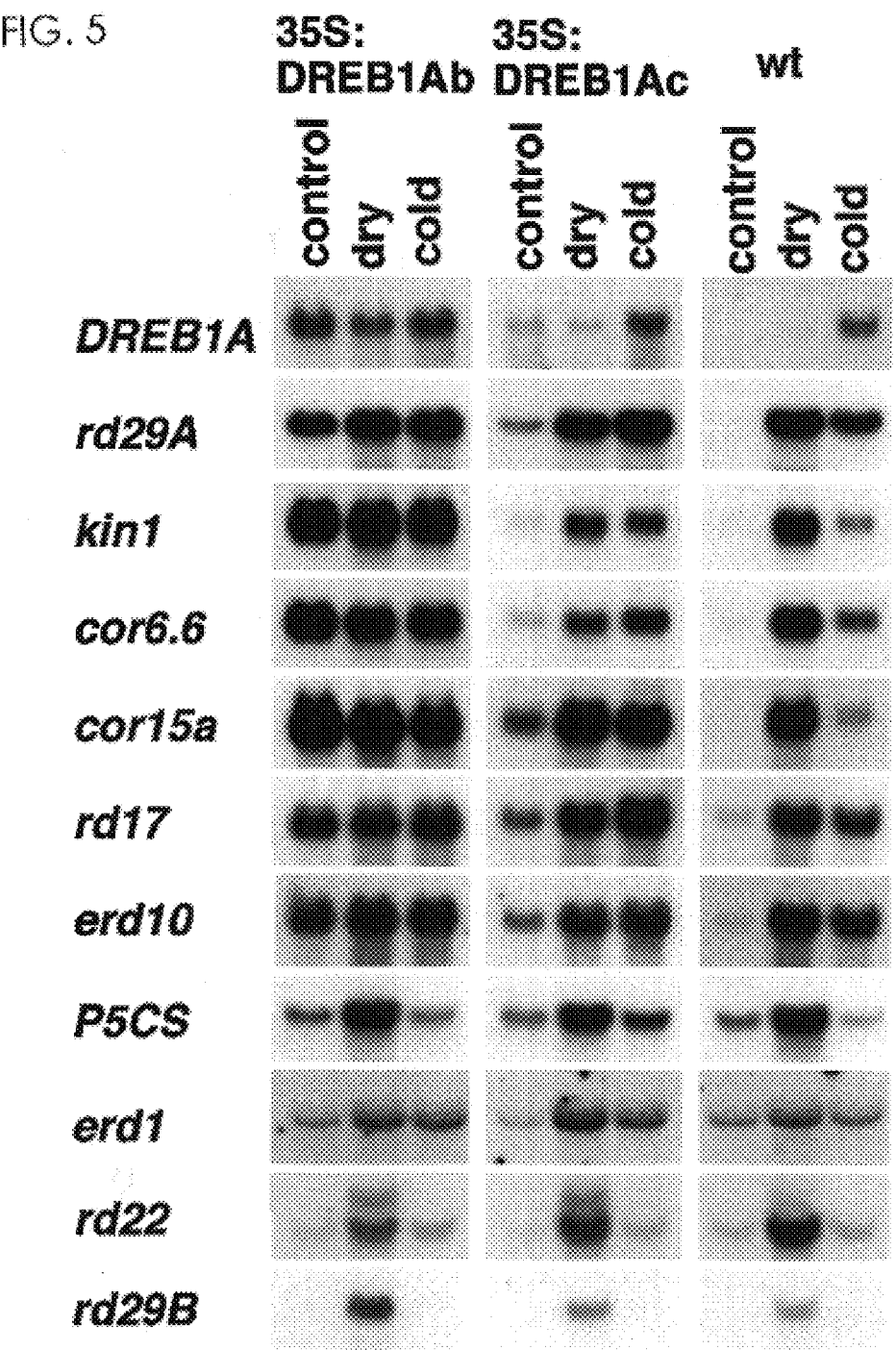
FIG. 5 presents electrophoresis photographs showing transcription levels of individual genes in DREB1A gene-introduced plants when stress is loaded.

(4) Identification of Genes Whose Expression has Been Altered by the Transgene and the Transcription Factor Encoded by the Transgene mRNA levels of those genes whose expression is considered to have been altered by the transgene DREB1A and the transcription factor encoded by this gene in the transformed plant were examined by Northern blot analysis. As a probe, a fragment of DREB1A, rd29A, kin1, cor6.6, cor15a, rd17, erd10, P5CS, erd1, rd22 or rd29B gene was used. In this Northern blot analysis, transformed and wild type *Arabidopsis thaliana* plants were used for comparing the expression of the above genes. Two grams each of plant bodies grown on GM agar medium for 3 weeks were exposed to dehydration stress and low temperature stress separately. Dehydration stress was given by pulling out the plant from the agar medium and drying it on a filter paper for 5 hr. Low temperature stress was given by retaining the plant at 4° C. for 5 hr. Total RNA was prepared separately from control plants which were given no stress, plants which were given dehydration stress and plants which were given low temperature stress. The resultant total RNA was subjected to electrophoresis. Then, expressing genes were assayed by Northern blot analysis. Generally, a transgene is located on the genome of a transformed plant in a similar manner. However, due to the difference in the locations on the genome, the expression of the transgene varies among transformants; this is a phenomenon called position effect. By assaying transformants by Northern blotting with a DNA fragment from the transgene as a probe, those transformants in which the transgene was expressed more highly were selected. Also, by using as a probe a DNA fragment of the above genes which are possibly involved in stress tolerance, those genes which exhibited changes in mRNA levels when DREB1A gene was introduced were identified (FIG. 5).

(5) Expression of Tolerance to Dehydration/Freezing Stress

Dehydration/freezing tolerance was investigated on *Arabidopsis thaliana* transformants which had been grown in 9 cm pots containing soil composed of vermiculite and perlite (50:50) for 3 weeks. As a control, *Arabidopsis thaliana* transformed with pBI121 not containing DREB1A gene was used. As to dehydration tolerance, water supply was stopped for 2 weeks and then plant survival was examined. As to freezing tolerance, the plant was maintained at −6° C. for 2 days and then grown at 22° C. for 5 days. Thereafter, its survival ratio was examined.

Figure 6:
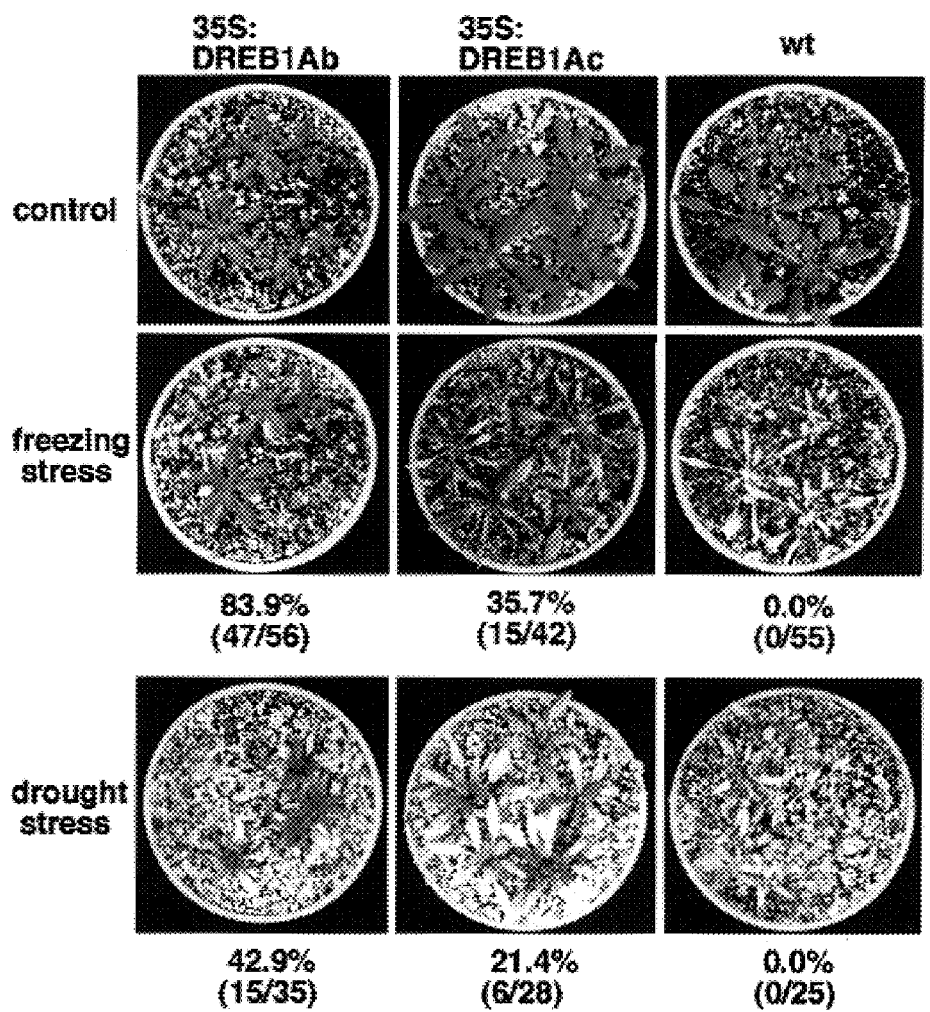
FIG. 6 presents photographs showing the growth of DREB1A gene-introduced plants when freezing stress or dehydration stress is given (morphology of organisms).

As a result, all the control plants were withered but the transgenic plants into which DREB1A gene was introduced exhibited a high survival ratio (FIG. 6). However, inhibition of growth and dwarfing were observed in these transgenic plants.

EXAMPLE 5

Creation of a Transgenic Plant Containing a Gene in which a DNA Encoding DREB1A Protein is Ligated Downstream of rd29A Gene Promoter (1) Construction of pBI29APNot Vector Containing rd29A Gene Promoter An rd29A promoter region (from −861 to +63 based on the translation initiation point of rd29A gene) with HindIII site added to both ends was prepared by PCR under the same conditions as described in (4) in Example 2 using the following primers: 5'-aagcttaagcttgccatagatgcaattcaatc-3' (SEQ ID NO:13) and 5'-aagcttaagcttttccaaagatttttttctttccaa-3' (SEQ ID NO: 14). The resultant PCR fragment was digested with HindIII and inserted into the HindIII site of a plant binary vector pBI101 (Clontech, Palo Alto, Calif., USA). β-glucuronidase gene (GUS) encoded in pBI101 was cut out with SmaI and SacI. Then, the resultant plasmid was ligated with SmaI-NotI-SacI polylinker. This plasmid was introduced into *E. coli* DH5a to prepare plasmid pBI29APNot.

(2) Construction of Plant Plasmid pBI29AP:DREB1A Using rd29A Gene Promoter

DREB1A gene was amplified by PCR using pSKDREB1A obtained in Example 1 as a template. Briefly, 5'-ggatccggatccatgaactcattttctgct-3' (SEQ ID NO: 15) was synthesized as a sense primer and 5'-ggatccggatcctaataactc-cataacgata-3' (SEQ ID NO: 16) as an antisense primer. BamHI site was introduced at 5' end of both primers so that the PCR fragment amplified can be ligated to the vector easily. The resultant PCR product was subjected to electrophoresis on 1% agarose gel. A band around 900-1000 bp was cut out from the gel. This gel fragment was placed in a fresh microtube, which was retained at 67° C. for 10 min to dissolve the gel. An equal volume of TE was added to the dissolved gel, mixed well and extracted with phenol. The resultant extract was centrifuged at 1,600×g for 3 min. Then, the aqueous layer was subjected to phenol extraction and phenol/chloroform extraction. To the resultant aqueous layer, cold ethanol was added to precipitate the PCR product.

Figure 7:
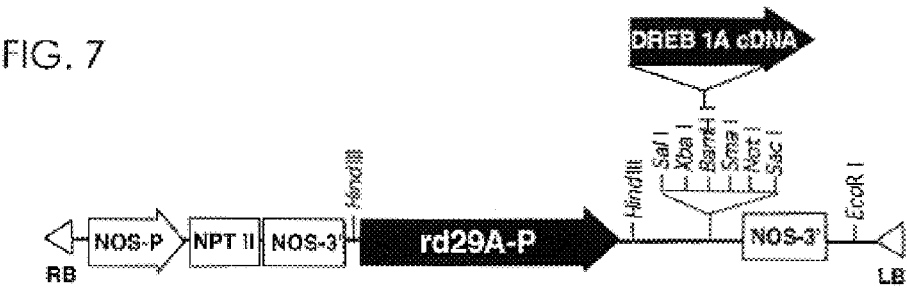
FIG. 7 is a diagram showing the structure of a rd29A gene promoter-containing recombinant plasmid to be introduced into a plant.

The resultant PCR product (10 μg) was dissolved in 30 μl of TE and digested with BamHI (20 U). After heating at 70° C. for 1 hr to deactivate BamHI, the digest was subjected to phenol extraction and ethanol precipitation to recover a DNA fragment containing DREB1A gene. Subsequently, this DNA fragment was ligated to the BamHI site of vector pBI29APNot. This recombinant plasmid was transformed into *E. coli* (DH5α), and the transformant was selected by kanamycin resistance. The selected transformant was cultured in LB medium. Then the plasmid pBI29AP:DREB1A was extracted and purified from the transformant (FIG. 7).

(3) Preparation of a Zygote *Agrobacterium* Containing Plant Plasmid pBI29AP:DREB1A Using the recombinant plasmid pBI29AP:DREB1A obtained in (2) above, a zygote *Agrobacterium* containing plant plasmid pBI29AP:DREB1A was prepared in the same manner as in (2) in Example 5.

(4) Gene Transfer into *Arabidopsis thaliana* by *Agrobacterium* Infection

Using the zygote *Agrobacterium* obtained in (3) above, plant plasmid pBI29AP:DREB1A was introduced into *Arabidopsis thaliana* in the same manner as in (3) in Example 5.

Figure 9A:
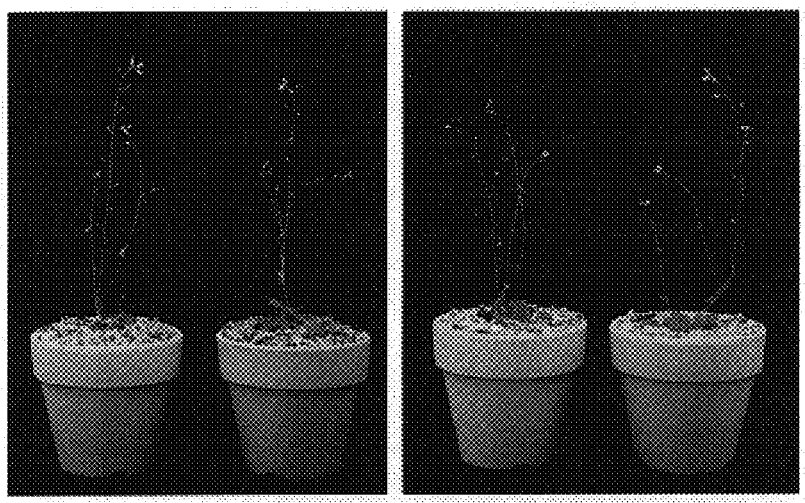
FIG. 9 presents photographs showing the growth of pBI29AP:DREB1A-introduced transgenic plants (morphology of organisms).
Figure 9B:
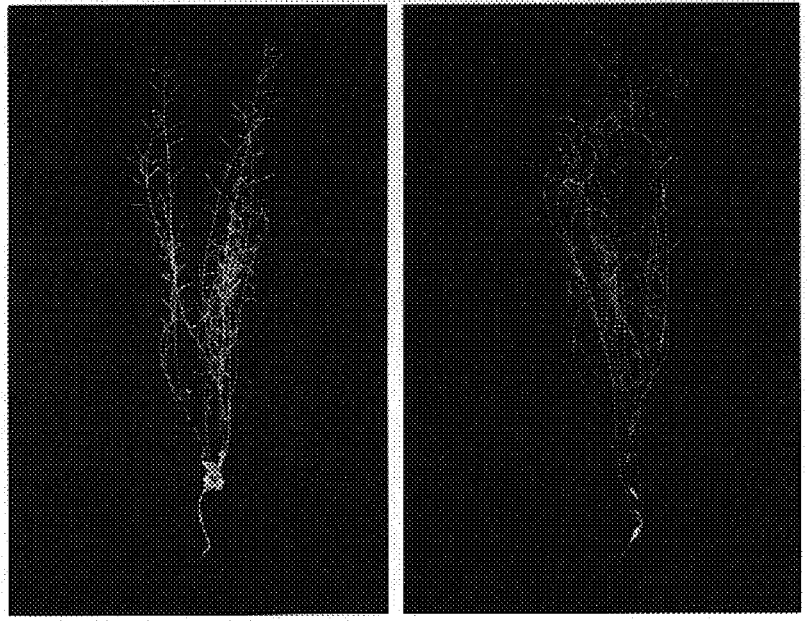

(5) Observation of the Growth and Dehydration/Freezing/Salt Stress Tolerance of the Transformant The transgenic *Arabidopsis thaliana* obtained in (4) above containing a plasmid in which DREB1A gene is ligated downstream of rd29A gene promoter, the transgenic *Arabidopsis thaliana* obtained in Example 5 containing a plasmid in which DREB1A gene is ligated downstream of CaMV35S gene promoter, and non-transformed *Arabidopsis thaliana* as a control were cultured under the same conditions. Then, their growth and survival ratios after the loading of dehydration, freezing or salt stress were examined. Briefly, each plant was planted in a 9 cm pot containing soil composed of vermiculite and perlite (50:50) and cultured outside. FIGS. 8 and 9 present photographs showing the growth of plants on day 35 (FIG. 8A and FIG. 9A) and on day 65 (FIG. 8B and FIG. 9B) of the cultivation. In the pBI35S:DREB1A-introduced transgenic plant, a remarkable inhibition of growth was observed though there was some difference in the degree of growth among plants (FIG. 8A and FIG. 8B). In contrast, almost no inhibition of growth was observed in the pBI29AP:DREB1A-introduced transgenic plant (FIG. 9A and FIG. 9B).

Figure 10:
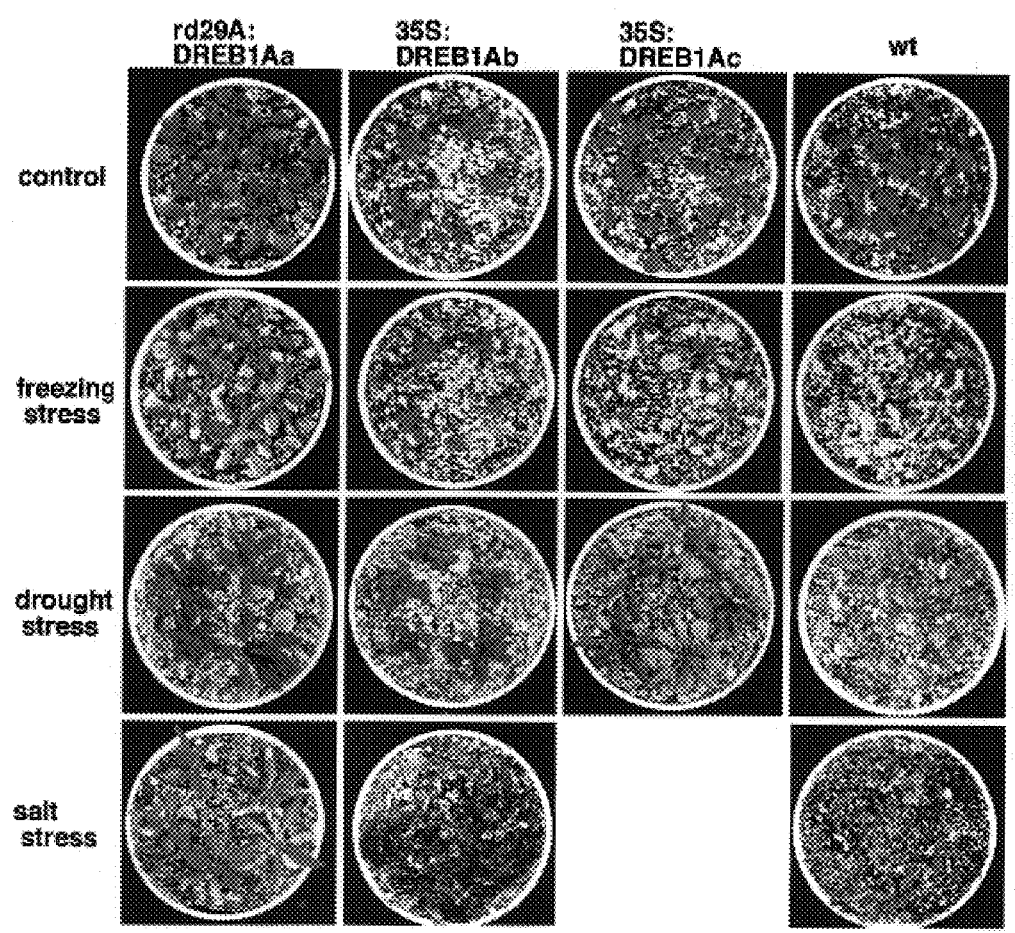
FIG. 10 presents photographs showing the survival of transgenic plants after stress loading (morphology of organisms).

Subsequently, their tolerance to stresses was examined. As to dehydration tolerance, water supply was stopped for 2 weeks and then plant survival was examined. As to freezing tolerance, plants were maintained at −6° C. for 2 days and then grown at 22° C. for 5 days. Thereafter, their survival ratios were examined. As to salt tolerance, plants were dipped in 600 mM NaCl for 2 hrs, then transferred to pots and grown there for 3 weeks. Thereafter, plant survival was examined. As a result, as shown in FIG. 10 and Tables 1 to 3, the control plants given dehydration or freezing stress were all withered. Only few control plants survived after the loading of salt stress. In the pBI35S:DREB1A-introduced transformant, the survival ratio varied among plants; those plants with higher expression of the introduced DREB1A gene exhibited higher tolerance. In contrast, in the pBI29AP:DREB1A-introduced transformant, the tolerance was almost equal among 43 plants analyzed. This transformant exhibited higher survival ratios than the pBI3SS:DREB1A-introduced transformant. Thus, it was found that the transgenic plant created by the invention has high levels of tolerance to dehydration, freezing and salt, and yet exhibits good growth.

TABLE 1

Survival Ratio of Transgenic Plants after the Loading of Freezing Stress

|  | No. of Individuals Survived | Total No. of Individuals | Survival Ratio (%) |
| --- | --- | --- | --- |
| rd29A:DREB1A | 143 | 144 | 99.3 |
| 35S:DREB1Ab | 47 | 56 | 83.9 |
| 35S:DREB1Ac | 15 | 42 | 35.7 |
| Wild type | 0 | 55 | 0.0 |

TABLE 2

Survival Ratio of Transgenic Plants after the Loading of Dehydration Stress

|  | No. of Individuals Survived | Total No. of Individuals | Survival Ratio (%) |
| --- | --- | --- | --- |
| rd29A:DREB1A | 52 | 80 | 65.0 |
| 35S:DREB1Ab | 15 | 35 | 42.9 |

TABLE 2-continued

Survival Ratio of Transgenic Plants after
the Loading of Dehydration Stress

|  | No. of Individuals Survived | Total No. of Individuals | Survival Ratio (%) |
|---|---|---|---|
| 35S:DREB1Ac | 6 | 28 | 21.4 |
| Wild type | 0 | 25 | 0.0 |

TABLE 3

Survival Ratio of Transgenic Plants
after the Loading of Salt Stress

|  | No. of Individuals Survived | Total No. of Individuals | Survival Ratio (%) |
|---|---|---|---|
| rd29A:DREB1A | 119 | 149 | 79.9 |
| 35S:DREB1Ab | 4 | 24 | 16.7 |
| Wild type | 4 | 29 | 13.8 |

EXAMPLE 6

Functional Analysis of *Arabidopsis* DREB2A Using
a Constitutive Active Form Mutant 1. Materials and Methods 1) Plant Materials Plants (*Arabidopsis thaliana* ecotype Columbia) were grown on germination medium agar plates for 3 weeks. For Northern analysis, 3-week-old plants were subjected to stress treatments and then frozen in liquid nitrogen for RNA extraction. For a stress tolerance test, 3-week-old plants were transferred onto soil and grown for one week. Stress treatments were carried out as described above. *Arabidopsis* T87 suspension cultured cells were maintained as described previously (Axelos et al., 1992, Plant Physiol. Biochem. 30, 123-128).

2) Transient Expression Experiments

Effector and reporter plasmids used in the transient trans-activation experiment regarding C-terminal deletion mutants of the DREB2A were constructed as described previously (Liu et al, 1998 Plant Cell 10, 1391-1406). Effector plasmids that encode the GAL4 DNA-binding domain fused to C-terminal region of DREB2A and a reporter plasmid that contains the GAL4 binding sequence were constructed as described above. Insert fragments used for construction of effector plasmids were amplified by PCR using the primer pairs shown in Table 4 (SEQ ID NOs:24-75).

Isolation of *Arabidopsis* T87 cell protoplasts and polyethylene glycol-mediated DNA transfection were performed as described previously (Abel and Theologis, 1994 Plant J. 5, 421-427). Five-day-old *Arabidopsis* T87 suspension cultured cells were collected by filtration and washed with water. Five grams of T87 cells were incubated with enzyme solution (0.4M mannitol, 5 mM MES-KOH (pH 5.7), 8 mM $CaCl_2$, 1% [w/v] Cellulase ONOZUKA R10 (Yakult), 0.5% [w/v] Macerozyme R10 (Yakult)) at room temperature for 2 hours with gentle agitation. Cells were passed through 125 μm nylon mesh, recovered by centrifugation at 450 g for 5 minutes at room temperature and washed twice in 30 ml of 0.4 mM mannitol, 70 mM $CaCl_2$, and 5 mM MES-KOH (pH 5.7). Finally protoplasts were resuspended in MaMg solution (0.4 M mannitol, 15 mM $MgCl_2$, 5 mM MES-KOH (pH 5.7)) and concentration was adjusted to $3 \times 10^6$ cell/ml. The isolated protoplasts were kept on ice until use. Plasmid DNAs used for protoplast transformation were prepared by using a QINGEN plasmid isolation kit (QIAGEN) and dissolved in 10 mM Tris-HCl (pH 8.0), and 1 mM EDTA at 1 μg/μL. One hundred μL of protoplast suspension was mixed well with 10 μL of effector plasmid, 10 μL of reporter plasmid and 5 μL of 35S:Luciferase internal control plasmid. Then PEG-CMS solution (0.4 M mannitol, 0.1 M $Ca(NO_3)_2$, and 40% [w/v] polyethylene glycol (PEG) 3350 (Sigma)) were added immediately to this protoplast-plasmid mixture and mixed well. Protoplasts were kept on ice for 20 minutes, and then diluted with 10 mL of 0.4 M mannitol, 125 mM $CaCl_2$, 5 mM KCl, 5 mM glucose, and 1.5 mM MES-KOH (pH 5.7). The diluted protoplasts were harvested by centrifugation at 450 g for 5 min at room temperature. Transformed protoplasts were resuspended in 2.5 mL of culture medium (0.4 M mannitol, 1× Murashige and Skoog [1962] basal medium) and cultured in the dark at 22° C. for up to 24 h.

GUS activity was assayed by fluorometric quantification of 4-methylumbelliferone produced from the glucuronide precursor as described above. Luciferase activity was assayed by measuring light emission of the reaction with a PikkaGene luciferase assay kit (Toyo-ink) using a lumino meter (Wallac 1420 ARVOsx).

TABLE 4

Primer pairs used for effector plasmid construction.

| Constructs | Forward primer 1 | Reverse primer 1 | Forward primer 2 | Reverse primer 2 |
|---|---|---|---|---|
| DREB2A 1-317 | SEQ ID NO. 24 | SEQ ID NO. 25 |  |  |
| DREB2A 1-281 | SEQ ID NO. 26 | SEQ ID NO. 27 |  |  |
| DREB2A 1-253 | SEQ ID NO. 28 | SEQ ID NO. 29 |  |  |
| DREB2A 1-165 | SEQ ID NO. 30 | SEQ ID NO. 31 |  |  |
| DREB2A 1-135 | SEQ ID NO. 32 | SEQ ID NO. 33 |  |  |
| DREB2AΔ136-165* | SEQ ID NO. 34 | SEQ ID NO. 35 | SEQ ID NO. 64 | SEQ ID NO. 65 |
| DREB2AΔ166-253* | SEQ ID NO. 36 | SEQ ID NO. 37 | SEQ ID NO. 66 | SEQ ID NO. 67 |
| DREB2AΔ254-281* | SEQ ID NO. 38 | SEQ ID NO. 39 | SEQ ID NO. 68 | SEQ ID NO. 69 |
| DREB2AΔ282-317* | SEQ ID NO. 40 | SEQ ID NO. 41 | SEQ ID NO. 70 | SEQ ID NO. 71 |
| DREB2AΔ136-253* | SEQ ID NO. 42 | SEQ ID NO. 43 | SEQ ID NO. 72 | SEQ ID NO. 73 |
| DREB2AΔ135-165, Δ318-335* | SEQ ID NO. 44 | SEQ ID NO. 45 | SEQ ID NO. 74 | SEQ ID NO. 75 |
| GAL4-BD-DREB2A 254-281 | SEQ ID NO. 46 | SEQ ID NO. 47 |  |  |
| GAL4-BD-DREB2A 254-317 | SEQ ID NO. 48 | SEQ ID NO. 49 |  |  |
| GAL4-BD-DREB2A 254-335 | SEQ ID NO. 50 | SEQ ID NO. 51 |  |  |
| GAL4-BD-DREB2A 136-253 | SEQ ID NO. 52 | SEQ ID NO. 53 |  |  |

TABLE 4-continued

Primer pairs used for effector plasmid construction.

| Constructs | Forward primer 1 | Reverse primer 1 | Forward primer 2 | Reverse primer 2 |
|---|---|---|---|---|
| GAL4-BD-DREB2A 136-335 | SEQ ID NO. 54 | SEQ ID NO. 55 | | |
| GAL4-BD-DREB2A 318-335 | SEQ ID NO. 56 | SEQ ID NO. 57 | | |
| GAL4-BD-DREB2A 166-253 | SEQ ID NO. 58 | SEQ ID NO. 59 | | |
| GAL4-BD-DREB2A 282-317 | SEQ ID NO. 60 | SEQ ID NO. 61 | | |
| GAL4-BD-DREB2A 282-335 | SEQ ID NO. 62 | SEQ ID NO. 63 | | |

*These fragments were generated by two-step PCR. First PCR used primer pair of the forward primer 1 and the reverse primer 1 or that of the forward primer 2 and the reverse primer 2 was carried out individually. Amplified fragments in the first PCRs were used for second PCR as template with the forward primer 1 and the reverse primer 2.

3) Plant Transformation

Plasmids used for the transformation of *Arabidopsis* were constructed with a mutant DREB2A fragment that lacks the region from amino acid residues 136 to 165. The fragment was digested by NotI from the Δ136-165 effector plasmid used in the transactivation experiment and inserted into the NotI site of pBluescript II SK-(Stratagene). Then the fragment was cut out from the plasmid with EcoRV and SacI, and subcloned into the SmaI-SacI site of pBE2113Not vector (Liu et al., 1998) in sense orientation. The constructed plasmid was introduced into *Agrobacterium tumefaciens* C58 by electro-transformation. Plant transformation was carried out as described above.

4) Microarray Analysis

Total RNA was isolated using the TRIZOL Reagent (Invitrogen) from 3-week-old plants having pBI121 or overexpressing a constitutive active form of DREB2A. mRNAs were prepared using the PolyATract mRNA isolation system III (Promega). Preparation of fluorescent probes, microarray hybridization, and scanning have been described previously (Seki et al., 2002, Plant J. 31, 279-292).

5) Northern Blot Analysis

Total RNA was extracted using the TRIZOL Reagent. Northern blot analysis was performed as described above.

2. Results

1) Transcriptional Activation Activity of Deletion Mutants of DREB2A

Figure 11:
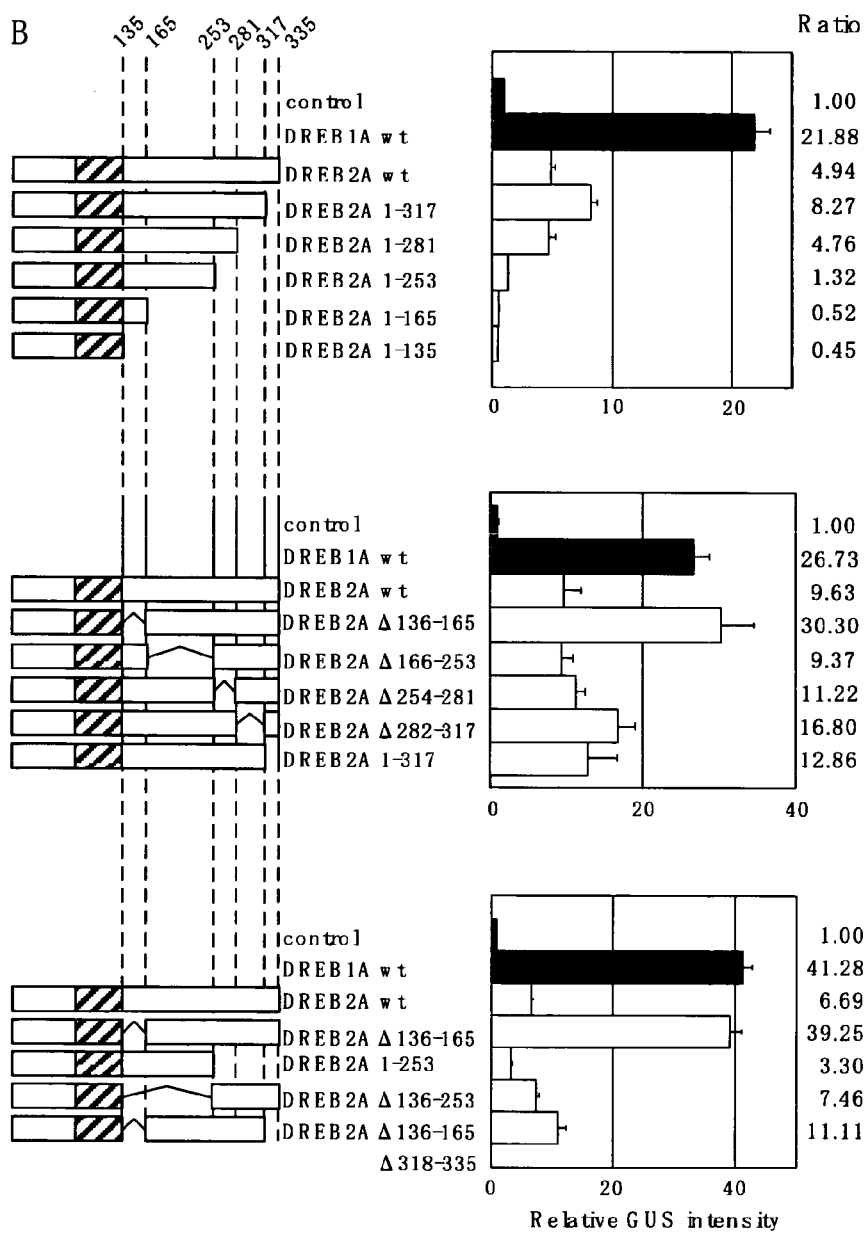
FIG. 11 shows the result of domain analysis of the C-terminal region of the DREB2A protein by using protoplasts prepared from *Arabidopsis* T87 cells.
(A) Schematic diagram of the reporter and effector constructs used in co-transfection experiments
(B) Transactivation of the rd29A promoter-GUS fusion gene by DREB1A, DREB2A, or C-terminal region deletion mutants of DREB2A

Because the C-terminal region of DREB2A is rich in acidic amino acids, the translational activation domain of the DREB2A protein has been predicted to exist in this region (Liu et al., 1998). To identify the translational activation domain, we carried out domain analysis of DREB2A in detail. Effector constructs containing a variety of C-terminal region deletion mutants of DREB2A were cotransfected with a β-glucuronidase (GUS) reporter construct driven by DRE sequences into protoplasts prepared from *Arabidopsis* T87 suspension cultured cells (FIG. 11). Overexpression of full length DREB2A resulted in five to nine times higher transactivation of the reporter gene as compared with the case of the empty effector control. Deletion from the C-terminal end to amino acid residue (a.a.) 254 (DREB2A: 1-253) decreased the DREB2A-mutant-dependent transcativation to a level as same as in the case of the control. On the other hand, an internal deletion mutant lacking the region between a.a. 136 and a.a. 253 showed same level of reporter gene activation as the full length of DREB2A. These results suggest that the translational activation domain exists between a.a. 254 and the C-terminal end.

Interestingly, deletion of the region between a.a. 136 and 165 significantly increased its activity. Expression of the reporter gene by DREB2A Δ136-165, which was over 30 times higher than the basal level, and more than 3 times higher than the case of the with full length of DREB2A. This induction was equivalent to the DREB1A effector construct. The region between a.a. 136 and 165 seems to have a negative roll in regulation of DREB2A activity. Deletions of the other regions did not result in significantly modulated transactivation activity.

2) The Region from 254 to the C-Terminal End Contains a Necessary and Sufficient Domain for Translational Activation, and the Region Between a.a. 136 and a.a. 165 has a Negative Role in DREB2A Activity.

Figure 12:
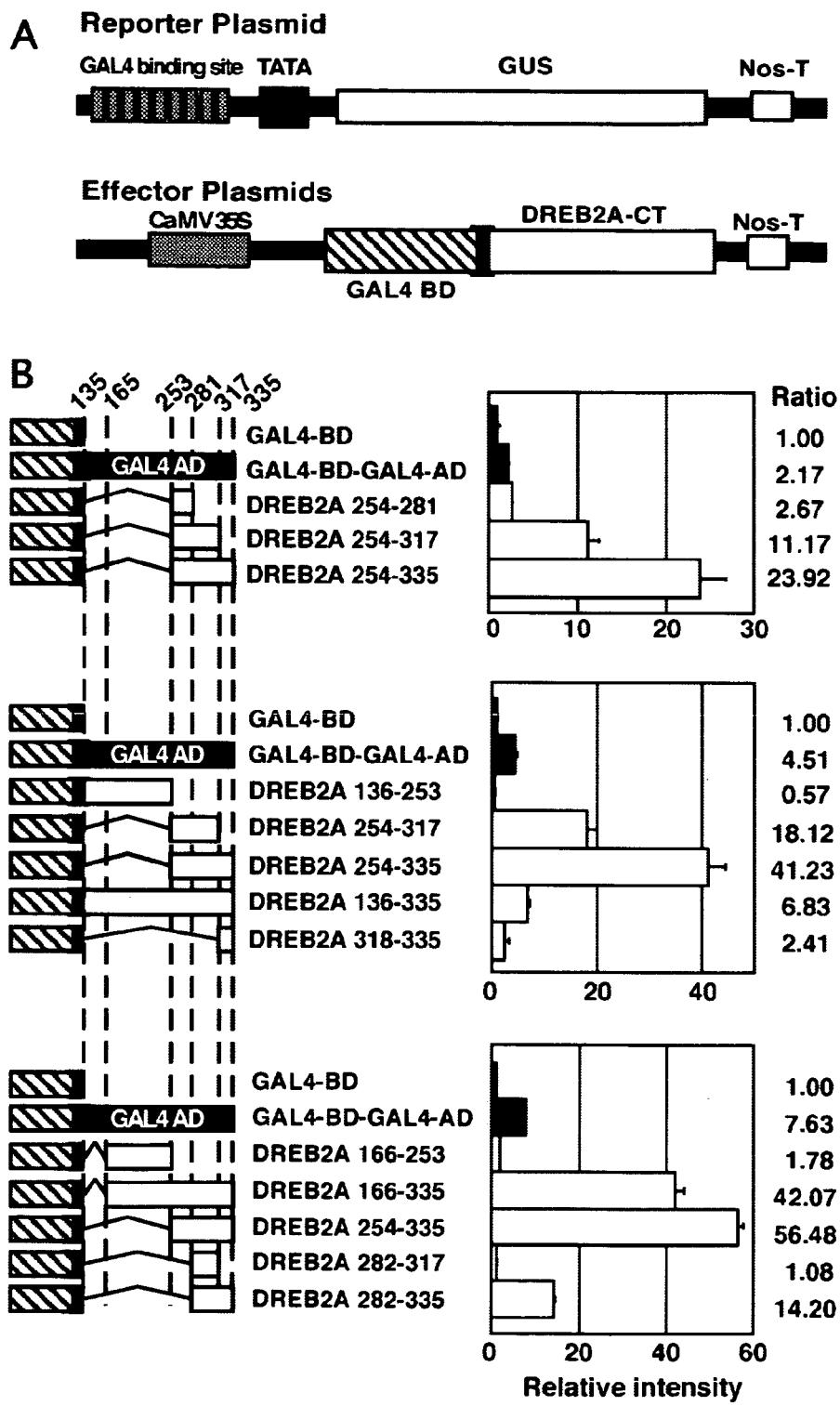
FIG. 12 shows a result of transcriptional activation with the C-terminal region of DREB2A fused to the GAL4-binding domain.
(A) Schematic diagram of the reporter and effector constructs
(B) Transactivation of the GAL4 binding site-GUS fusion gene by the fusion proteins of the GAL4 DNA binding domain and the GAL4 activation region or C-terminal regions of the DREB2A protein as indicated by numbers of amino acid residues

For further domain analysis of DREB2A, we prepared effector constructs that contained variety of fragments from DREB2A fused to the GAL4 DNA binding domain (GB) (Ma et al, 1988, Nature 334, 631-633). The effector plasmid was co-transfected into protoplasts of the *Arabidopsis* T87 cell with a reporter plasmid that contained nine copies of a GAL4-binding site fused to the minimal promoter of CaMV35S and the GUS reporter gene (FIG. 12). As in the case of the results in FIG. 11, effector constructs of GB-DREB2A 136-253 and GB-DREB2A 166-253 that lacked the region from a.a. 254 the to C-terminal end of DREB2A did not induce expression of the reporter gene. GB-DREB2A 254-335, the effector construct containing the region from a.a. 254 to the C-terminal end, induced highest expression of the reporter gene among all effector constructs. This region consists of three sub-regions. Each sub-region could not or could only weakly stimulate the expression of the reporter gene when it fused to the GAL4 binding domain independently (FIG. 12B, GB-DREB2A 254-281, 282-317 and 318-335), and a deletion of at least one sub-domain significantly decreased activity of the GUS reporter compared with GB-DREB2A 254-335 (FIG. 12B, GB-DREB2A 254-317 and 282-335). Even if the fragment of GB-DREB2A 254-335 was extended toward the N-terminal such as GB-DREB2A 166-335 or 136-335, no further increase of reporter activity was observed. Although the effector construct, GB-DREB2A 166-335, induced reporter gene expression at almost the same level as GB-DREB2A 254-335, the transactivation by GB-DREB2A 136-335 that contained the region a.a. 136-165 was about six times lower than that by GB-DREB2A 254-335. These results indicate that the region between a.a. 254 and a.a. 335 is a necessary and sufficient activation domain of DREB2A, and that the region between a.a. 136-165 negatively controls translational activation ability of the DREB2A protein.

3) Overexpression of the Constitutive Active Form of DREB2A in *Arabidopsis*

Figure 13:
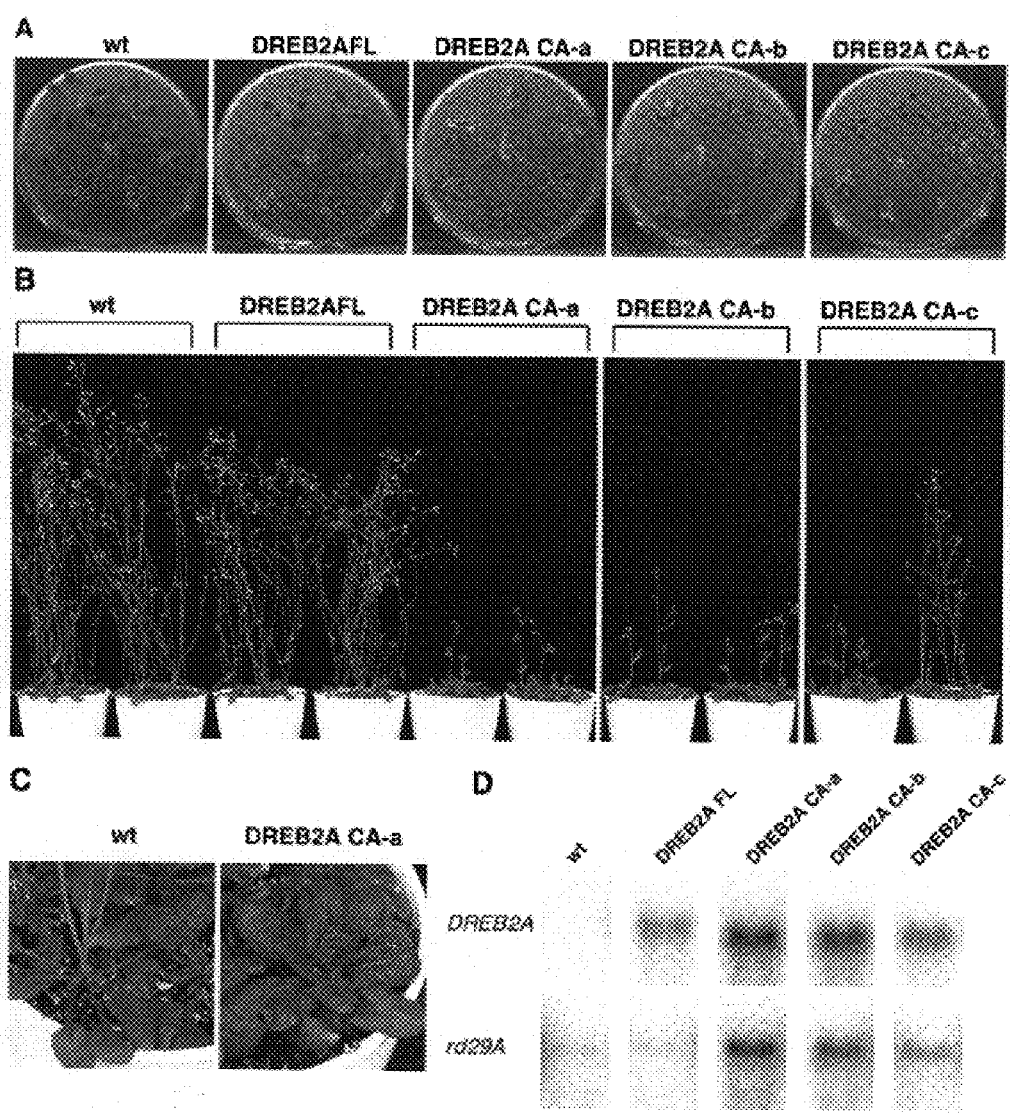
FIG. 13 shows effects of overexpressing the constitutive active form of DREB2A in transgenic plants.

To analyze the function of DREB2A, the DREB2A deletion mutant, DREB2A Δ136-165 (FIG. 11) that showed highest activity in the transient transactivation experiments was overexpressed in *Arabidopsis* plants. The gene encoding the constitutive active form of DREB2A was overexpressed under the control of the CaMV35S promoter (Mitsuhara et al., 1996). The tobacco mosaic virus (TMV) Ω sequence (Gallie et al., 1987) was inserted upstream of the mutant DREB2A fragment to increase the translation level. Fifty five transgenic *Arabidopsis* plants were generated by using the vacuum infiltration method. Expression levels of the transgene in transgenic T2 plants were analyzed by northern blot analysis, and we selected three lines of DREB2A, CA-a, -b and -c, that showed strong, moderate and weak transgene expression, respectively, for further analysis. Growth and expression of the DREB2A target gene of T2 transformants were confirmed. The growth patterns of the DREB2A CA plants were compared with control plants having the pBI121 vector (wt) and DREB2A FL plants overexpressing the full length DREB2A cDNA. All the DREB2A CA plants showed retarded growth (FIGS. 13A and B). The severest growth retardation was observed in the DREB2A CA-a plants in which the transgene was strongly expressed, and the levels of growth retardation of DREB2A CA-c in which the transgene was weakly expressed were mild. By contrast, no growth retardation was observed in DREB2A FL overexpresssing the full length of DREB2A.

The DREB2A CA plants had a round shape and slightly dark green leaves with short leaf stems. These phenotypes appeared in DREB2A CA-a to a greater extent than in the case of DREB2A-c (FIG. 13C). The environment stress-responsive gene, rd29A, has the DRE motives in the promoter region and it is confirmed that the DREB2A protein can bind to this DRE sequence as described above. Accumulation levels of the rd29A mRNA were increased in correlation with the expression levels of the constitutive active form of DREB2A.

4) Microarray Analysis of the Transgenic *Arabidopsis* Plants Overexpressing the Constitutive Active Form of DREB2A In order to understand which genes were under the control of DREB2A, we compared accumulation of mRNAs of ~7000 genes between wild type plants and DREB2A CA plants by using an *Arabidopsis* full-length cDNA microarray. Cy3-labeled and Cy5-labeled cDNA probes were prepared by using mRNA that was isolated from DREB2A CAs and control plants without stress treatment, respectively. These probes were hybridized with the cDNA microarray, and the expression profiles of the ~7000 genes were analyzed. The experiments were repeated three times and the genes regarding which signal intensities exceeded 2000 in at lest one experiment were further analyzed. We choose genes that showed an expression ratio 0.5 or more times greater in the DREB2A CA-a plants than in wild type plants as candidates for the DREB2A target genes (Table 5).

TABLE 5

Significantly upregulated transcripts in DREB2A CA-a plants[a]

| Gene Name[b] | AGI code[c] | Ratio[d] DREB2A CA-a | DREB1A[e] | DRE[g] | ABRE[g] | Description[h] |
|---|---|---|---|---|---|---|
| rd29A | At5g52310 | 16.0 | 14.7[f] | −265 to −260<br>−215 to −210<br>−158 to −153<br>−121 to −116 | −55 to −50 | Late embryogenesis abundant protein |
| AtGolS3 | At1g09350 | 14.3 | 10.6[f] | −800 to −805<br>−376 to −381<br>−772 to −777 | −265 to −260 | Galactinol synthase |
| rd29B | At5gS2300 | 12.5 | 2.8 | −162 to 157 | −168 to −163<br>−63 to −58<br>−704 to −709<br>−77 to −82<br>−35 to −30 | Late embryogenesis abundant protein |
| RAFL06-13-J20 | At1g52690 | 12.0 | 0.8 | −37 to −32 | −220 to −225<br>−625 to −620<br>−617 to −622<br>−228 to −223<br>−190 to −185 | Late embryogenesis-abundant protein |
| rd17 | At1g20440 | 11.2 | 8.3[f] | −985 to −980<br>−151 to 146<br>−956 to 951 | −909 to −904<br>−330 to −335 | Dehydrin |
| cor15A | At2g42540 | 10.7 | 13.1[f] | −350 to −345<br>−173 to −168<br>−402 to −407 | −121 to −116<br>−113 to −118<br>−289 to −294<br>−60 to −55 | Late embryogenesis abundant protein |
| RAFL02-04-GO3 | At4g33720 | 10.3 | 0.8 | | −16 to −11<br>−195 to −200 | Pathogenssis-related protein 1 |
| AtMT-K | At3g09390 | 10.0 | 2.0 | −172 to −167 | | Metallothionein-like protein |
| RAFL05-13-A17 | At1g32860 | 9.4 | 1.4 | −61 to −56<br>−605 to −600 | −572 to −577 | Unknown protein |
| RAFL05-16-B15 | At1g69870 | 9.0 | 2.5 | −332 to −327 | −92 to −87<br>−190 to −185 | Unknown protein |
| RAFL06-16-L13 | At5g54960 | 7.0 | 1.6 | −288 to −293<br>−357 to −362 | −934 to −929 | Pyruvate decarboxylase |
| RAFL05-17-B13 | At1g01470 | 6.3 | 7.1[f] | −404 to −399<br>−56 to −51<br>−369 to −374 | −631 to −636<br>−132 to −137<br>−88 to −93 | Late embryogenesis-abundant protein |

TABLE 5-continued

Significantly upregulated transcripts in DREB2A CA-a plants[a]

| | | Ratio[d] | | | | |
|---|---|---|---|---|---|---|
| Gene Name[b] | AGI code[c] | DREB2A CA-a | DREB1A[e] | DRE[g] | ABRE[g] | Description[h] |
| RAFL04-10-D13 | At2g23120 | 6.0 | 5.0[f] | −117 to −112 | −65 to −60<br>−85 to −90 | Unknown protein |
| RAFL05-21-K17 | At5g54170 | 5.6 | 0.8 | | | Membrane related protein-like |
| kin1 | At5g15960 | 5.5 | 11.7[f] | −109 to −104 | −346 to −351<br>−67 to −62<br>−132 to −137 | Late embryogenesis abundant protein |
| RAFL04-1B-BO7 | At5g62350 | 5.5 | 4.6[f] | −550 to −545<br>−30 to −25<br>−182 to −177 | | Unknown protein |
| RAFL03-05-EO8 | At3g53990 | 5.3 | 2.3 | −968 to −973<br>−181 to −186 | | Unknown protein |
| AtGRP7 | At2g21660 | 5.2 | 3.3[f] | −77 to −72 | −292 to −297 | Glycine-rich RNA binding protein |
| kin2 | At5g15970 | 5.2 | 3.3[f] | −121 to −116 | −54 to −59<br>−62 to −57<br>−71 to −76<br>−79 to −74<br>−145 to −149<br>−365 to −370 | Late embryogenesis abundant protein |

[a]mRNAs from DREB2A CA-a and pBI121 plants were used for preparation of Cy3-labeled and Cy5-labeled cDNA probes. These cDNA probes were mixed and hybridized with the cDNA microarray. In this study, we used lambda DNA as internal control because its fluoresence level is almost the same in both the plants.
[b]Gene names are full-length cDNA clones (Seki et al., 2002).
[c]AGI code for cDNAs used in this study.

[d] $\dfrac{\text{Fluorescence Intensity (FI) of each cDNA of 35S:DREB2A CA-a plants}}{\text{FI of each cDNA of pBI121 plants}} \div \dfrac{\text{FI of lambda DNA of DREB2A CA-a plants}}{\text{FI of lambda DNA of pBI121 plants}}$

[e]Maruyama et al., 2003.
[f]DREB1A target genes. (Maruyama et al., 2003).
[g]DRE sequence (RCCGAC) or ABRE sequence (ACGTGY) observed in 1000 nucleotides existing upstream of the 5'-termini of the longest cDNA clones isolated are listed. Numbers indicate the numbers of nucleotides beginning at the 5'-termini of the longest cDNA clones isolated. Minus sign means that the nucleotide exist upstream of the 5'-termini of the putative transcription site.
[h]Descriptions are cited from MIPS database.

Nineteen genes exhibited expression that increased more than 5 times in DREB2A CA-a plants than in wild type plants. Among DREB2A CA-a, b and c, expression levels of these genes correlated with the accumulation of mRNA of the constitutive active form of DREB2A (data not shown). Many of these genes are those encoding water-stress-related proteins such as LEA protein. To confirm whether the promoter regions of the nineteen genes contained the DRE and ABA responsive element (ABRE) or not, we surveyed the promoter region from ATG to 1 kb upstream. Seventeen of the nineteen genes had the DRE sequence(s), fifteen genes had the ABRE sequence(s) and fourteen genes had both cis-elements in their promoter region. These facts suggest that most of DREB2A target genes are important in water stress tolerance and therefore these genes are regulated by both the DREB pathway and the ABA pathway. On the other hand, interestingly, only ten genes in the list were identified as the DREB1A target genes.

Figure 14:
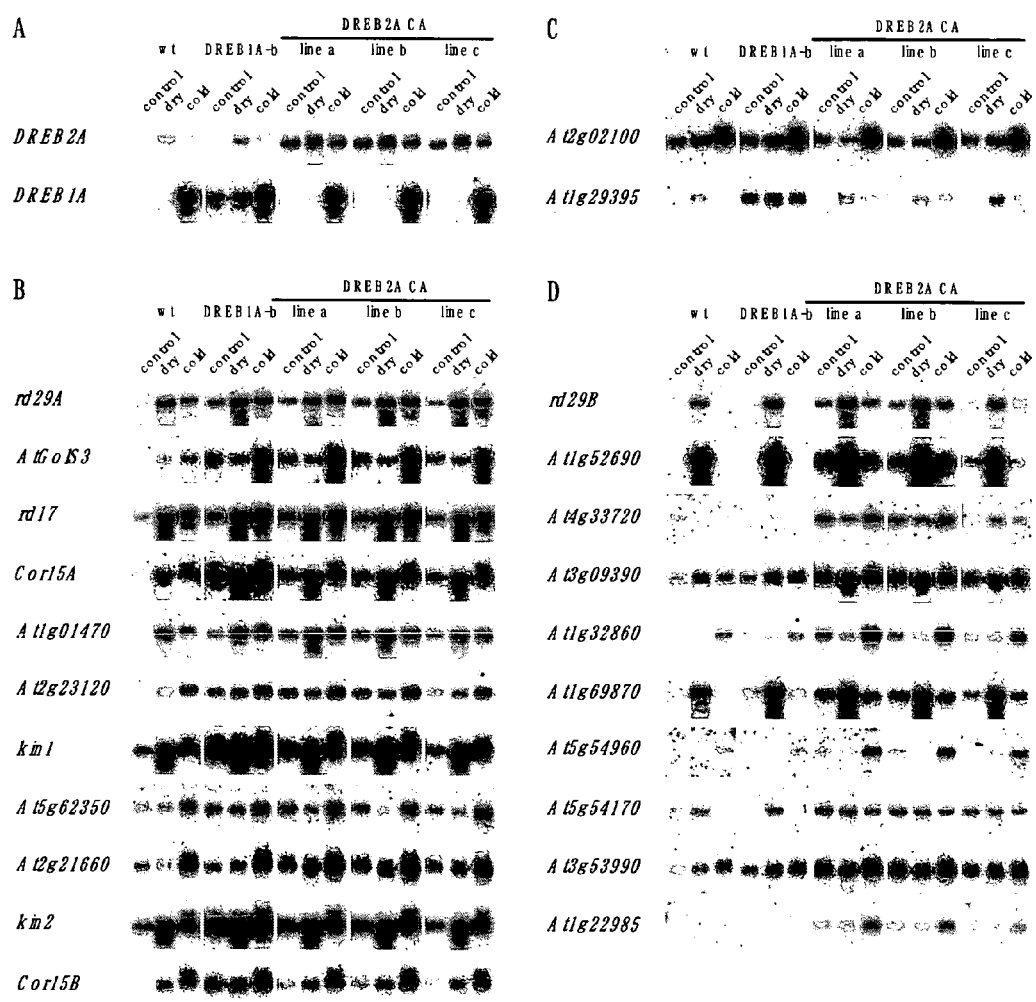
FIG. 14 shows photographs showing expression of the DREB target genes in plants carrying pBI121 (wt), the 35S:constitutive active form of DREB2A (35S:DREB2A CA) and 35S:DREB1A constructs.

For further analysis of the genes that up-regulated by overexpression of the constitutive active form of the DREB2A, we carried out the Northern blot analysis. The total RNAs isolated from plants of the wild type, DREB1A-b and DREB2A CA a-c with or without stress treatment of 4° C. for 5 hours or dehydration for 5 hours were used for the Northern blot analysis (FIG. 14). Accumulations of mRNA of eleven genes were increased in both the DREB1A-b and the DREB2A CAs plants compared with the wild type plants (FIG. 14B). DREB1A-b was the transgenic plants overexpressing DREB1A under the control of the CaMV35S promoter. The DREB1A-b plants showed moderate phenotypic change among the DREB1A overexpressors. Though AtGolS3 has the DRE sequence in the promoter region, it is known that this gene is cold inducible but not drought inducible. Thus the promoter region of this gene is predicted to contain a novel cis-element that negatively regulates the gene expression under drought conditions (Taji et al., 2002, Plant J. 29, 417-426). The expression of AtGolS3 in the DREB2A CA plants was stronger in control and cold treatment, and weaker in dry treatment. This fact strongly supports the hypothesis described above, and the AtGolS3 may not be the target gene of DREB2A physiologically, though the DREB2A protein can bind to the AtGolS3 promoter region. In spite of the fact that At2g02100 and At1g29395 are target genes of DREB1A and these have DREs in their promoter regions, expression of these genes was not induced in the DREB2A CA plants compared with the wild type plants. However, expression of At1g29395 was induced by drought in the wild type plants. Four of the ABRE existed in the promoter region of the At1g 29395, and thus ABA seems to be involved with drought inducible expression of At1g29395. Results of the northern blot analysis regarding the genes for which expression was induced in DREB2A CA plants but not in DREB1A-b plants were showed in FIG. 14D. Most of these genes are shown inducible. In particular, rd29B, At1g52690, At3g09390, At1g69870 and At1g22985 showed distinct drought specific gene expression. It is suggested that regulation of the expression of these genes via DRE is regulated by DREB2A, but not by DREB1A. Because the promoter region of At5g54170 did not contain the DRE sequence, drought specific gene expression of this gene may be an indirect affect of DREB2A. At1g22985 encodes a transcriptional factor containing the ERF/AP2 domain. The genes like the At1g22985 seem to control the DREB2A target genes that do not contain DRE in their promoter region, such as At5g54170. At4g33720 did not show stress inducible gene expression. Moreover, this gene did not contain DRE in its promoter region. Thus, an increase of expression of At4g33720 was probably an indirect and artificial effect of the strong expression of the constitutive active form of DREB2A.

Figure 15:
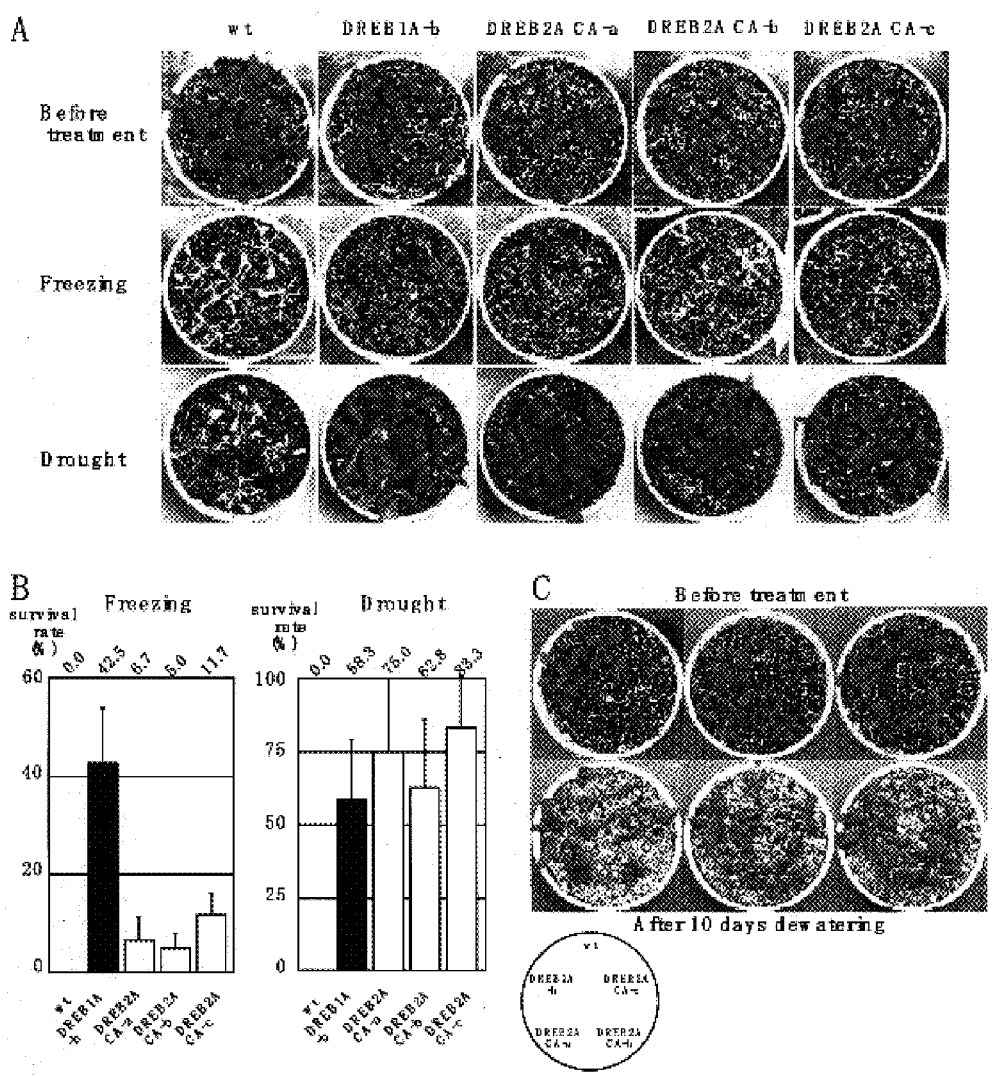
FIG. 15 shows freezing and drought tolerance of the plants carrying the 35S:constitutive active form of DREB2A and 35S:DREB1A constructs.
(A) Photographs of plants before and after stress treatments
(B) Survival rates of plants exposed to freezing and drought stress
(C) Photographs of plants before and after 10-day dewatering when they were planted in single pot: In another experiment The patent or application file contains at least one drawing executed in color. Copies of this patent or patent application publication with color drawings will be provided by the Office upon request and payment of the necessary fee.

5) Freezing and Drought Stress Tolerance of the Transgenic *Arabidopsis* Plants Overexpressing the Constitutive Active Form of DREB2A The tolerance for freezing and drought stresses of the DREB2A CA plants were compared with those of the DREB1A-b and wild type plants (FIG. 15). The plants were grown on germination medium agar plates for 3 weeks, then transferred onto pots that filled with soil and grown for one week at 22° C. For drought stress treatment, water was withheld from the plants for 2 weeks. They were then watered and grown under control conditions for 3 days. This treatment blighted all wild type plants, whereas about 60% of the DREB1A-b plants survived this treatment. As in the case of the DREB1A-b, 62.8%-83.3% of the DREB2A CA plants survived this treatment. For the freezing stress treatment, plants were exposed to a temperature of −6° C. for 30 h, and returned to 22° C. for 5 days. This treatment blighted all wild type plants, whereas about 40% of the DREB1A-b plants survived this treatment. By contrast to the drought stress tolerance, just 5.0%-11.7% of the DREB2A CA plants remained after freezing treatment. In another experiment, wild type plants and transgenic plants (DREB1A-a, DREB2A CA-a, DREB2A CA-b, and DREB2A CA-c) were planted in single pot and their survival after 10-day dewatering was compared. Wild type plants blighted after 10-day dewatering, whereas transgenic plants grew well. These results indicate that the target genes of DREB2A play an important role in acquirement of tolerance to drought stress, but these are not sufficient for resistance to freezing stress.

3. Discussion

Though overexpression of DREB1A under the control of the CaMV35S promoter caused phenotype changes in the transgenic plants, transgenic plants overexpressing full-length cDNA of DREB2A showed almost same phenotype as wild type plants. Therefore, it seems that the translated DREB2A protein is an inactive form and the DREB2A protein requires some kind of modification for its activation.

In this study, it is revealed that the translational activation domain of the DREB2A protein exists at the C-terminal, in the a.a. 254-335 region. The fusion protein of this region and GAL4 DNA binding domain showed significant transactivation of the reporter gene (FIG. 12, GD-DREB2A 254-335). These results suggest that this region has transcriptional activation ability without any modification and there is another region that negatively controls activity of the DREB2A protein. Actually, the deletion of the a.a. 136-165 region significantly increased DREB2A activity. This fact indicates that this region has a negative roll in regulation of DREB2A protein activity. The a.a. 254-335 and a.a. 136-165 regions are encoded by the positions 572-661 and 926-1171 of SEQ ID NO: 3, respectively.

Figure 4:
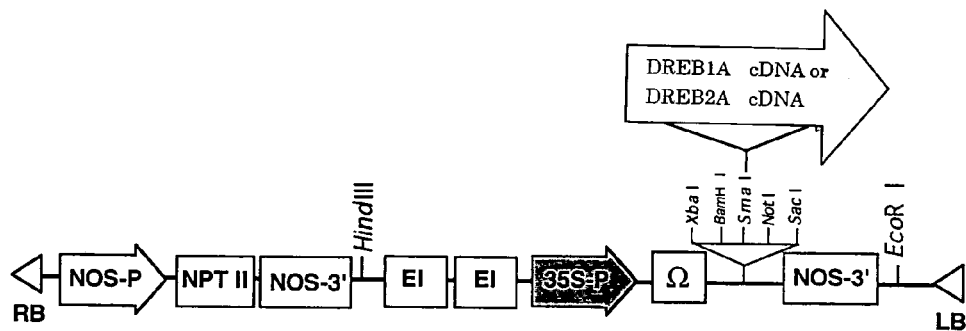
FIG. 4 is a diagram showing the structure of a CaMV35S promoter-containing recombinant plasmid to be introduced into a plant.

DNA binding domain and a nuclear localization signal (NLS) in N-terminal region of DREB2A gene are also essential for exertion of transactivation activity of DREB2A. In fact, effecter constructs containing various C-terminal region deletion mutants of DREB2A gene shown in FIG. 11 contain the DNA binding domain and nuclear localization signal in N-terminal region. Also, effecter constructs shown in FIG. 12 contain exogenous GAL4 DNA binding domain, which includes NLS therein, instead of endogenous DNA binding domain and NLS of DREB2A gene. Liu et al. (Plant Cell. 1998 August; 10(8): pp. 1391-406) describes: "We searched DNA and protein databases for sequences homologous to those of the DREB1A and DREB2A proteins and found that each DREB protein has a conserved DNA binding domain of 58 amino acids present in a large family of plant genes for DNA binding proteins, including EREBPs of tobacco and AP2 of *Arabidopsis* (FIG. 4). The deduced amino acid sequences of DREB1A and DREB2A showed no significant sequence identity except in the conserved DNA binding domain. However, each DREB protein contains a basic region in its N-terminal region that might function as a nuclear localization signal and an acidic C-terminal region that might act as an activation domain for transcription. These data suggest that each DREB cDNA encodes a DNA binding protein that might function as a transcriptional activator in plants."

In order to determine the positions of NLS and DNA binding domain of DREB2A, we have conducted the following analysis and database search. An analysis by a PSORT program (psort.ims.u-tokyo.ac.jp) revealed that the DREB2A protein has bipartite nuclear localization signals (NLS) at N-terminal region as RKRK from amino acid position 19 and KKRK from amino acid position 52. A search of CDD (www.ncbi.nlm.nih.gov/Structure/cdd/cdd.shtml) revealed that the DREB2A protein has three DNA binding domains within the regions of a.a. 78-138, a.a. 77-137, and a.a. 79-135, respectively.

The DREB1A protein and the DREB2A proteins have appeared to recognize the same cis-element, DRE. However, it is revealed in this study that the set of the DREB1A target genes and the set of the DREB2A target genes were not completely consistent. Moreover, although the Cor15A and B were recognized by both DREBs, expression levels of these genes were significantly different between DREB1A-b plants and DREB2A CA-a (FIG. 14B). This inconsistency regarding the sets of the target genes between DREB proteins was perhaps a reason for the fact that freezing tolerance of the DREB2A CA plants was weaker than the DREB1A-b plants, although these two kinds of transgenic plants showed same levels of drought stress tolerance. In the previous report, we revealed that both the DREB1A and the DREB2A proteins recognized the same core sequence of RCCGAC (Sakuma et al., 2002). However, recently we have elucidated that the DREB1A protein has the most affinity to an RCCGACxT sequence by detailed analysis of the promoter region of the DREB1A target genes (Maruyama et al., 2003). To find the reason why the sets of the target genes of DREB1A and DREB2A did not coincide, we analyzed the promoter region within 500 bp upstream from ATG of the genes whose expression level in microarray analysis is increased more than 5 times in the DREB2A CA-a plants but increased less than 3 times in the DREB1A-b plants compared with that in the wild type plants. Eight of the DRE sequences were found, but only two (25%) DRE sequences have the RCCGACxT sequences. The DREB2A protein probably can bind to a DRE sequence other than RCCGACxT and control the expression of genes the expression of which is hardly controlled by DREB1A. We have also attempted to identify the sequence that is a prerequisite to binding of the DREB2A protein. However, remarkable bias of the nucleotide abundance ratio was not observed. To achieve this goal, more DREB2A-specific target genes may be necessary.

Expression of DREB2A is induced by drought and high-salinity stress and the DREB2A protein specifically binds to the DRE element, and therefore, DREB2A is expected to be involved with ABA independent water stress inducible gene expression. However, distinct evidence to confirm this hypothesis has not been obtained because overexpression of DREB2A did not induce any phenotypic change in the transgenic plants. Also, the DREB2 gene family consists of at least two members (DREB2A and DREB2B) and thus the function of the DREB2 genes may be redundant. In addition, most of water stress inducible genes have both the DRE and the ABRE in their promoter region and ABA signals may be also transmitted to the DRE via DREB1D/CBF4. This study clearly showed that DREB2A certainly plays a roll in the dehydration stress inducible signal transduction pathway. This fact means that we have obtained a novel tool for the molecular improvement of plant tolerance to environmental stresses.

All publications, patents and patent applications cited herein are incorporated herein by reference in their entirety.

EFFECT OF THE INVENTION

According to the present invention, there is provided a transgenic plant containing a gene in which a DNA coding for a protein that binds to a stress responsive element and regulates the transcription of genes located downstream of the element is ligated downstream of a stress responsive promoter, the transgenic plant having improved tolerance to environmental stresses (such as dehydration, low temperature and salt) and being free from dwarfing.

What is claimed is:

1. A transgenic plant comprising a DNA that encodes a protein consisting of the amino acid sequence as shown in SEQ ID NO: 4 with the deletion of amino acids from positions 136-165 thereof, said DNA being operably linked downstream of a stress responsive promoter.

2. The transgenic plant of claim 1, wherein said protein can bind to said stress responsive promoter.

3. The transgenic plant of claim 1, wherein the protein consisting of the amino acid sequence as shown in SEQ ID NO: 4 with the deletion of amino acids from positions 136-165 thereof provides at least a three fold increase in transactivation activity of a reporter gene when compared with that of a full length DREB2A protein.

4. An isolated nucleic acid molecule that encodes a DREB2A protein as shown in SEQ ID NO:4 with the deletion of amino acids from positions 136 to 165 thereof.

5. A transgenic plant which comprises a DNA comprising the isolated nucleic acid molecule of claim 4, the DNA operably linked downstream of a stress responsive promoter.

6. A transgenic plant comprising a DNA that encodes a protein consisting of a fragment of the amino acid sequence as shown in SEQ ID NO: 4 with the deletion of amino acids from positions 136-165 thereof, wherein said fragment comprises the amino acid sequence of positions 254-335 and DNA binding domain and a nuclear localization signal, said DNA being operably linked downstream of a stress responsive promoter.

7. A transgenic plant comprising a DNA comprising the nucleotide sequence shown in SEQ ID NO: 3 with the deletion of the nucleotides from positions 572-661 thereof, said DNA being operably linked downstream of a stress responsive promoter.

8. The transgenic plant of claim 7, wherein a protein encoded by said DNA can bind to said stress responsive promoter.

9. The transgenic plant of claim 7, wherein said DNA encodes a protein that can bind to said stress responsive promoter.

10. An isolated nucleic acid molecule as shown in SEQ ID NO: 3 with the deletion of the region from nucleotide positions 572-661 thereof.

11. A transgenic plant which comprises a DNA comprising the isolated nucleic acid molecule of claim 10, said DNA being operably linked downstream of a stress responsive promoter.

* * * * *